United States Patent
Kotoku et al.

(10) Patent No.: US 11,475,578 B2
(45) Date of Patent: Oct. 18, 2022

(54) METHOD FOR ANALYZING BEHAVIOR OF CELL, AND USE THEREOF

(71) Applicant: TEIKYO UNIVERSITY, Tokyo (JP)

(72) Inventors: Junichi Kotoku, Tokyo (JP); Takuya Hirose, Tokyo (JP); Daisuke Nanba, Tokyo (JP); Emi Nishimura, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 0 days.

(21) Appl. No.: 17/253,812

(22) PCT Filed: Jun. 19, 2019

(86) PCT No.: PCT/JP2019/024225
§ 371 (c)(1),
(2) Date: Dec. 18, 2020

(87) PCT Pub. No.: WO2019/244917
PCT Pub. Date: Dec. 26, 2019

(65) Prior Publication Data
US 2021/0201508 A1    Jul. 1, 2021

(30) Foreign Application Priority Data
Jun. 19, 2018 (JP) .............................. JP2018-116303

(51) Int. Cl.
*C12Q 1/04* (2006.01)
*G06T 7/277* (2017.01)

(52) U.S. Cl.
CPC ............... *G06T 7/277* (2017.01); *C12Q 1/04* (2013.01); *G06T 2207/30024* (2013.01)

(58) Field of Classification Search
CPC ........... G06T 7/277; G06T 2207/30024; G06T 2207/20084
See application file for complete search history.

(56) References Cited

U.S. PATENT DOCUMENTS

| 6,026,174 A | 2/2000 | Palcic et al. |
| 2007/0026574 A1 | 2/2007 | Beatson et al. |
| 2010/0046823 A1 | 2/2010 | O Ruanaidh et al. |

FOREIGN PATENT DOCUMENTS

| JP | 2007-303886 A | 11/2007 |
| JP | 2014-083042 A | 5/2014 |

(Continued)

OTHER PUBLICATIONS

Li, Kang et al., "Cell population tracking and lineage construction with spatiotemporal context", Medical Image Analysis, 2008, vol. 12(2008), pp. 546-566; Cited in the specification.

(Continued)

*Primary Examiner* — Sam Bhattacharya
(74) *Attorney, Agent, or Firm* — WHDA, LLP

(57) ABSTRACT

Even for the case where cells such as human epidermal keratinocytes form a dense colony, or the case where cell contours are indefinite, each of the cells is automatically tracked with high precision, and behavior of each cell is analyzed with good precision. There is provided a method for analyzing behavior of a cell, which comprises a detection step of detecting positions of a plurality of cells for every frame of time-lapse images, while determining whether a candidate region extracted from the frame is a cell region by using a dictionary containing image data of cell nuclei; and a tracking step of tracking each cell by using a state space model using position of a most adjacent cell within a predetermined distance from a predicted position as observation data. When any cell is not found within a certain distance from the predicted position, data are considered missing.

10 Claims, 16 Drawing Sheets

(56) References Cited

FOREIGN PATENT DOCUMENTS

| JP | 2014-085950 | A | 5/2014 |
|---|---|---|---|
| JP | 2017-023055 | A | 2/2017 |
| JP | 6090770 | B2 | 3/2017 |
| JP | 2017-140006 | A | 8/2017 |
| JP | 6218208 | B2 | 10/2017 |
| JP | 2018-019632 | A | 2/2018 |
| WO | 2017/174267 | A1 | 10/2017 |

OTHER PUBLICATIONS

Chenouard, Nicolas et al., "Objective comparison of particle tracking methods", Nature Methods, vol. 11, No. 3, Mar. 2014, pp. 281-289; Cited in the specification.
Nanba, Daisuke et al., "Cell motion predicts human epidermal stemness", The Journal of Cell Biology, 2015, vol. 209, No. 2, pp. 305-315; Cited in the specification and cited in IPRP dated Dec. 22, 2020.
International Preliminary Report on Patentability (Form PCT/IB/373) issued in counterpart International Application No. PCT/JP2019/024225 dated Dec. 22, 2020, with Form PCT/ISA/237. with translation (8 pages).
Liu, Zichuan et al., "NucleiNet: A Convolutional Encoder-decoder Network for Bio-image Denoising", Med. Biol. Soc., Jul. 2017, pp. 1986-1989; Cited in IPRP dated Dec. 22, 2020.
Moon, Inkyu et al., "Automated tracking of temporal displacements of a red blood cell obtained by time-lapse digital holographic microscopy", Applied Optics, Jan. 20, 2016, vol. 55, No. 3, pp. A86-A94; Cited in IPRP dated Dec. 22, 2020.
Kaakinen, M et al., "Automatic detection and analysis of cell motility in phase-contrast time-lapse images using a combination of maximally stable external regions and Kalman filter approaches" Journal of Microscopy, 2014, vol. 253, Issue 1, pp. 65-78; Cited in IPRP dated Dec. 22, 2020.
Wang, Mengmeng et al., "Automated Tracking of Cells From Phase Contrast Images by Multiple Hypothesis Kalman Filters", ICASSP (IEEE), 2015, pp. 942-946; Cited in IPRP dated Dec. 22, 2020.
Higuchi, The Journal of the Institute of Electronics, 2005, vol. 88, No. 12, pp. 989-994; Cited in IPRP dated Dec. 22, 2020.
Esteve et al., "Gradient convergence filters and a phase congruency approach for in vivo cell nuclei detection", Machine Vision and Applications, 2012, vol. 23, No. 4, pp. 623-638, cited in EP Extended European Search Report dated Jun. 20, 2022. (16 pages).
Extended (Supplementary) European Search Report dated Jun. 20, 2022, issued in counterpart EP application No. 19821590.7. (14 pages).

[Fig.1]
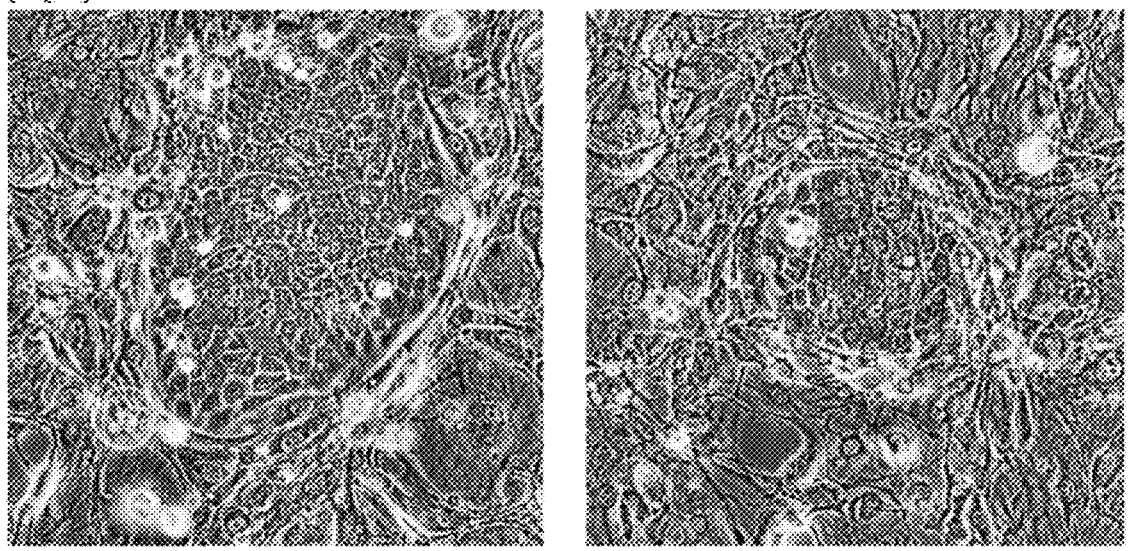
[Fig.2]
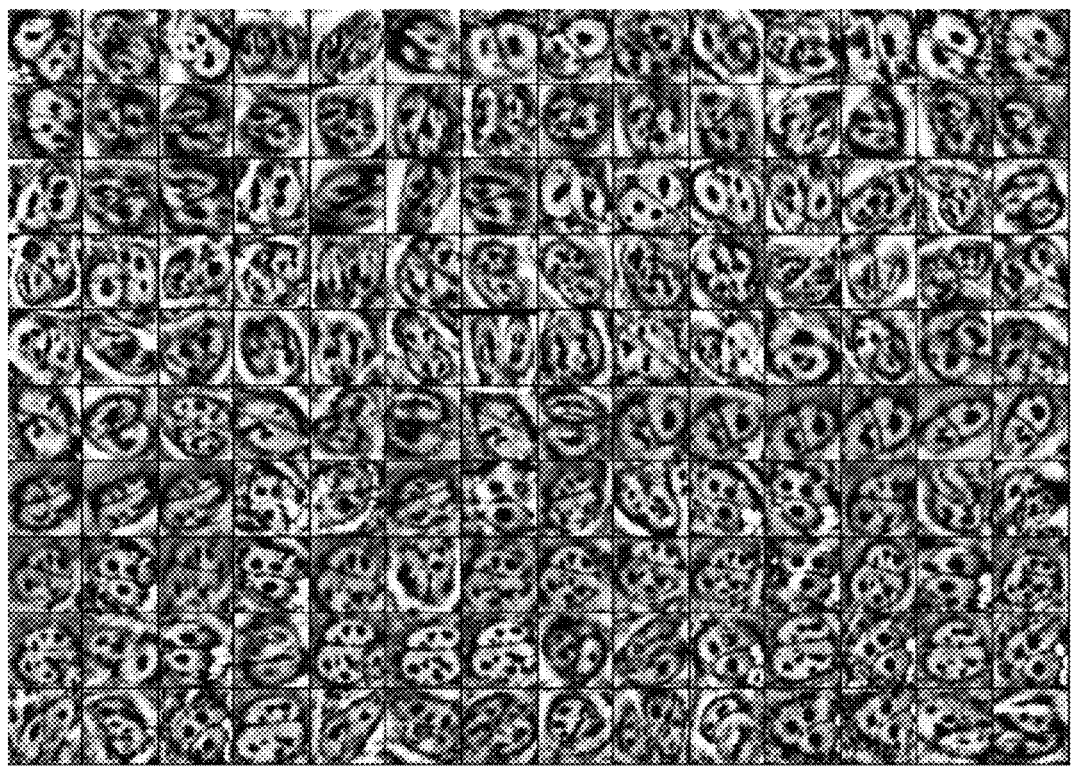

[Fig.3-1]
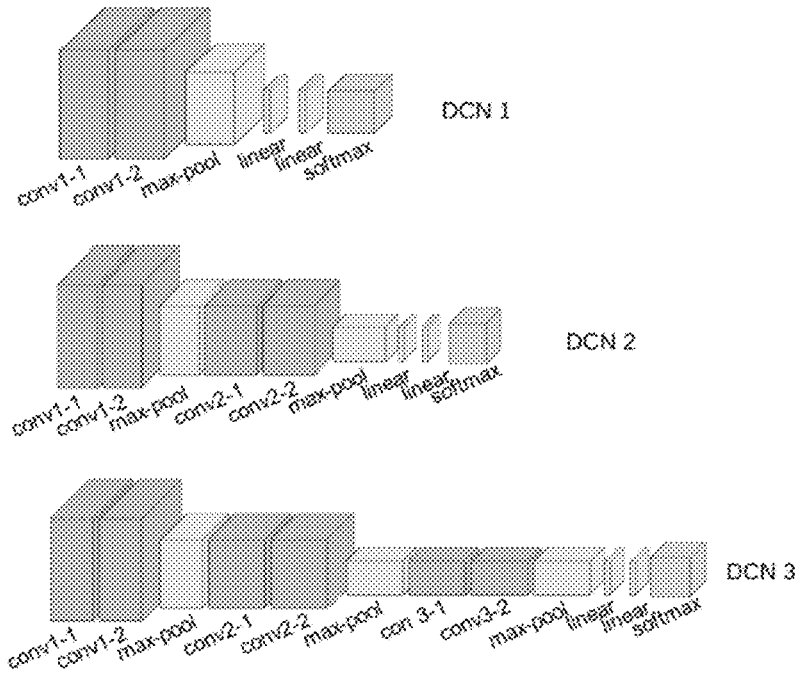
[Fig.3-2]
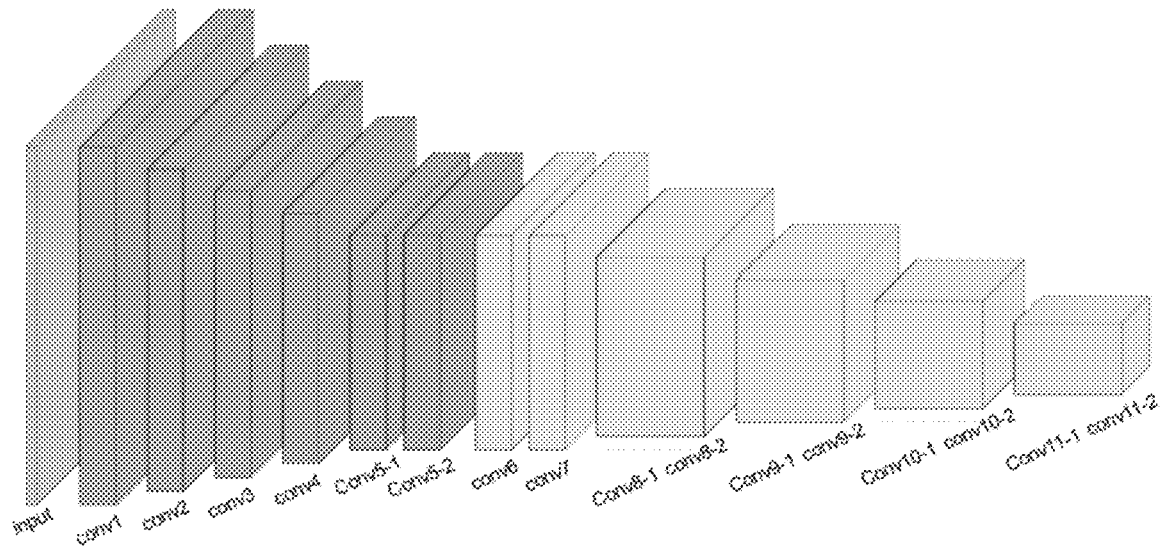

[Fig.3-3]
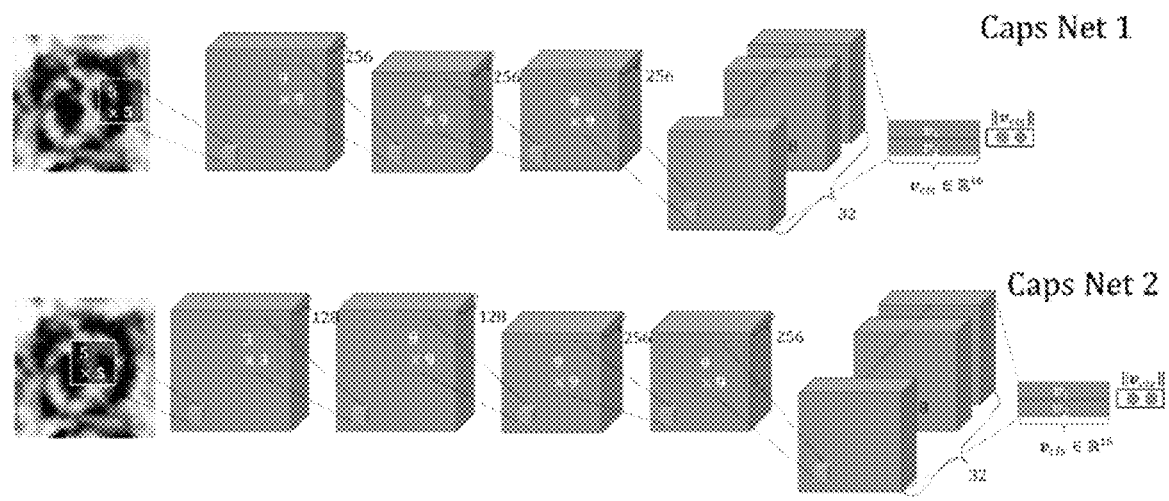

[Fig.4-1]
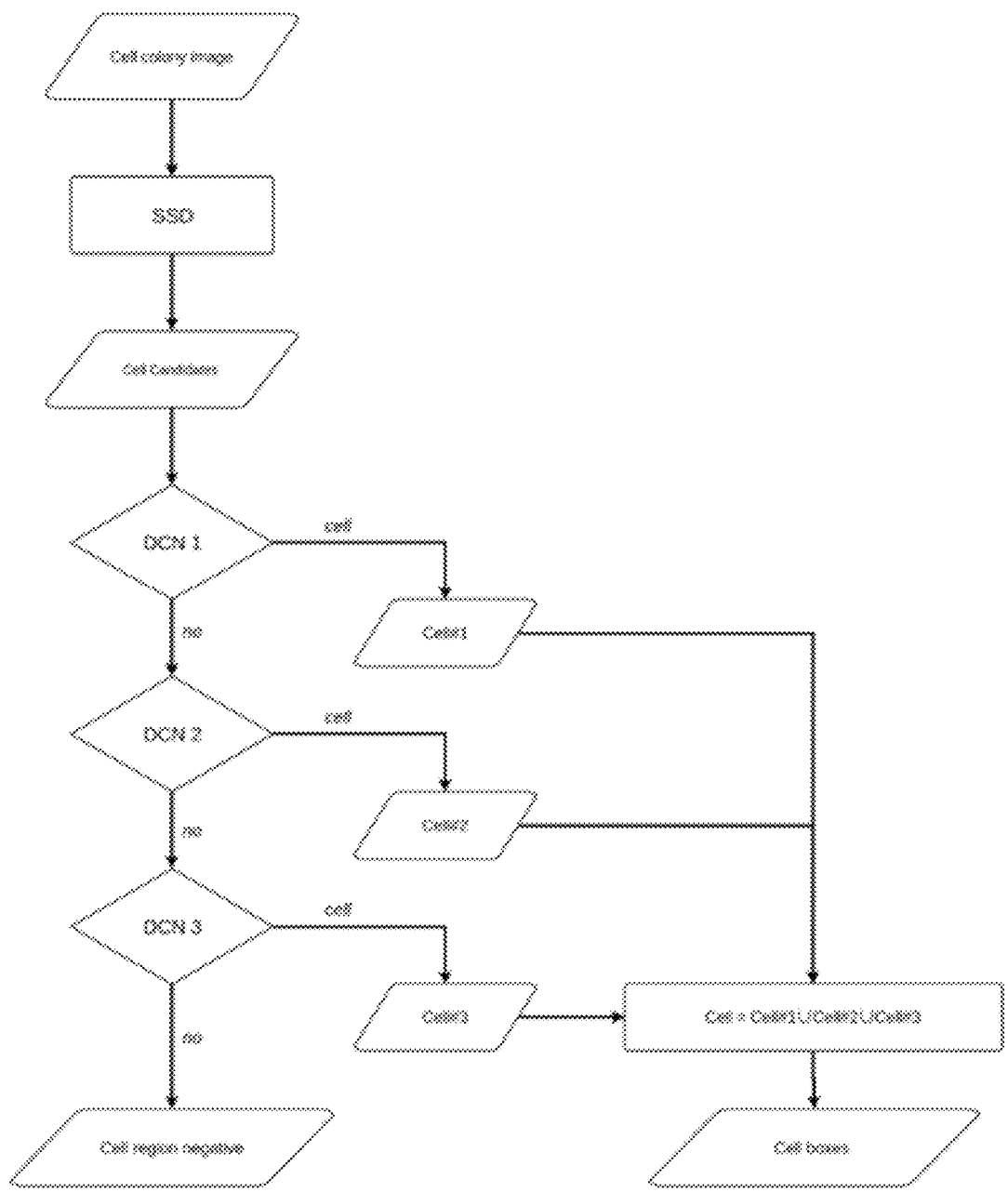

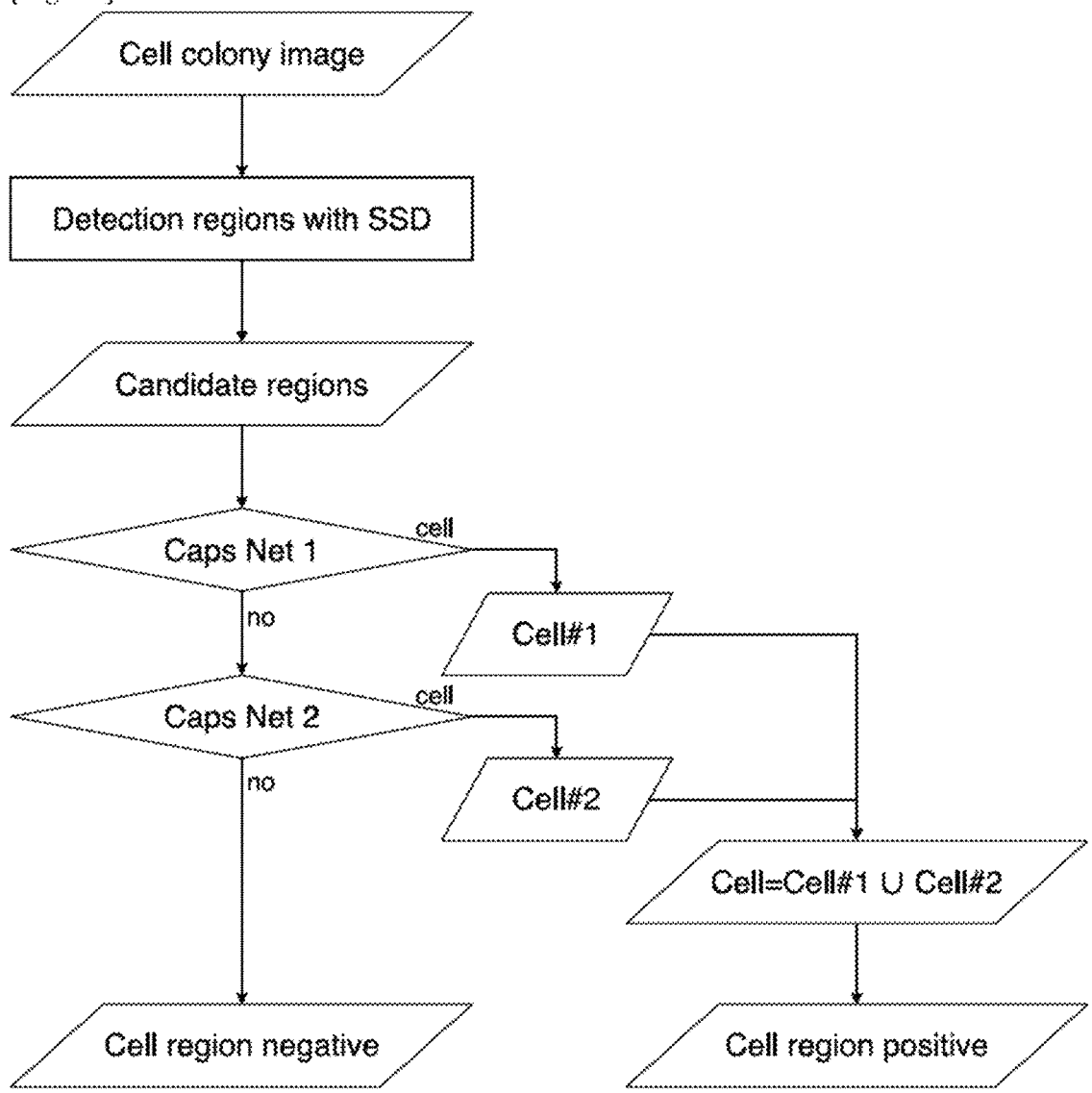

[Fig.5-1]
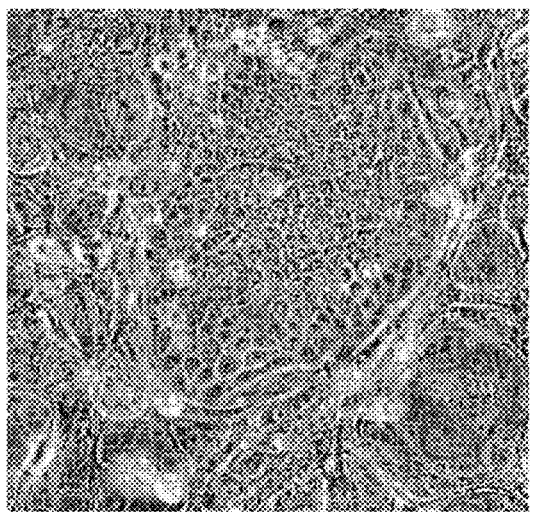
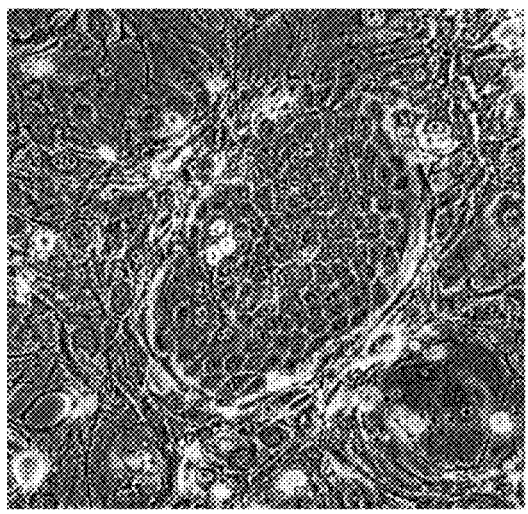
[Fig.5-2]
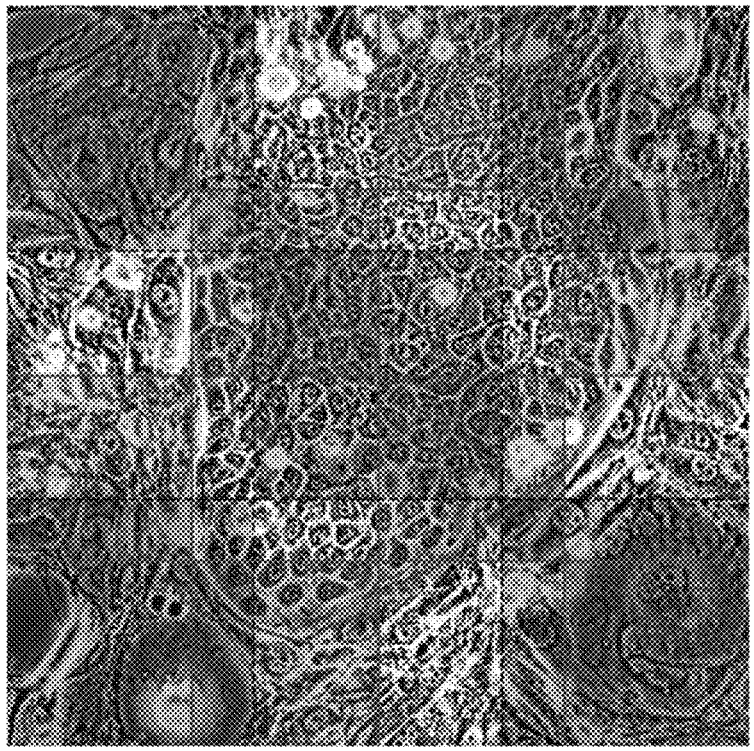

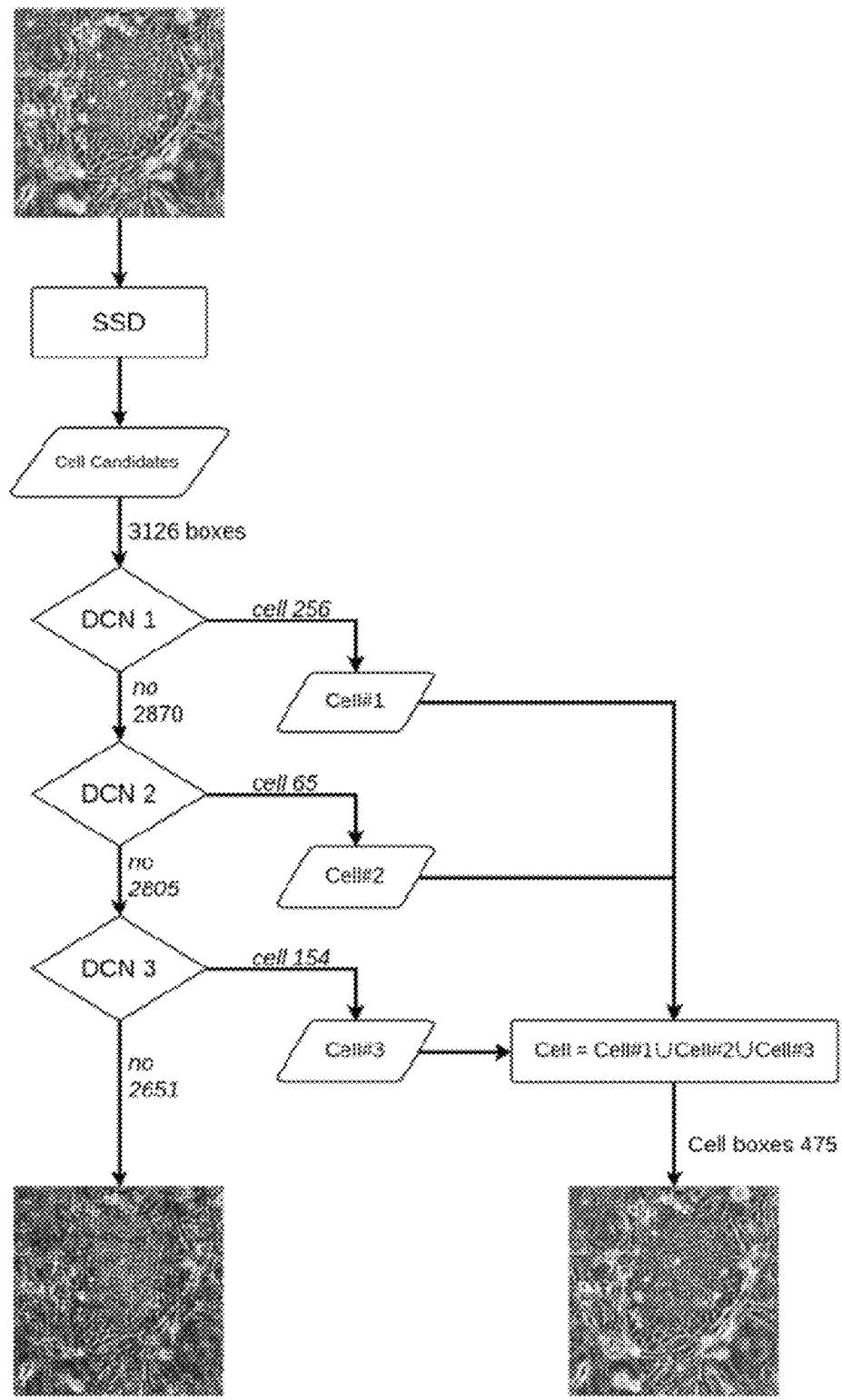
[Fig.6]

[Fig.7]
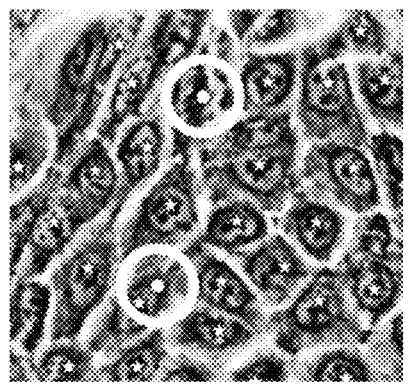
[Fig.8]
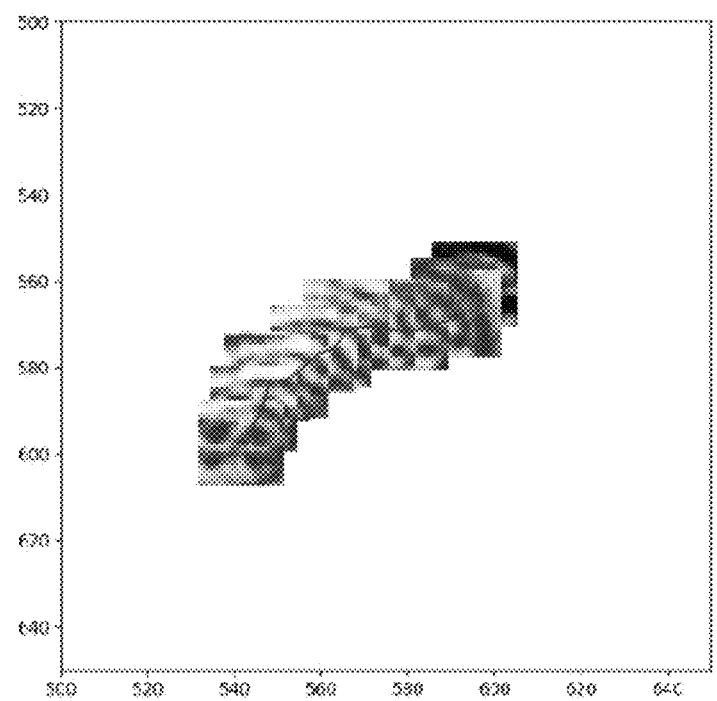

[Fig.9]
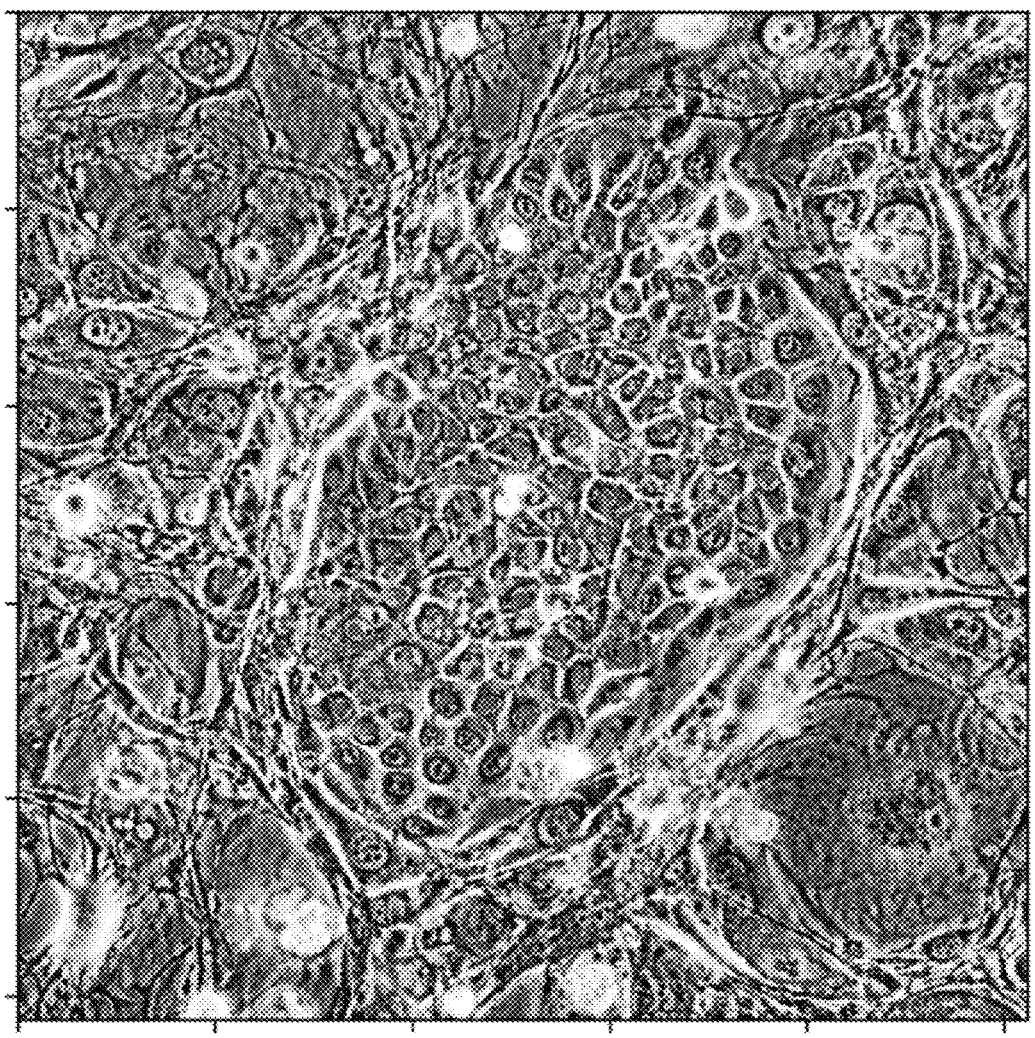

[Fig.10]
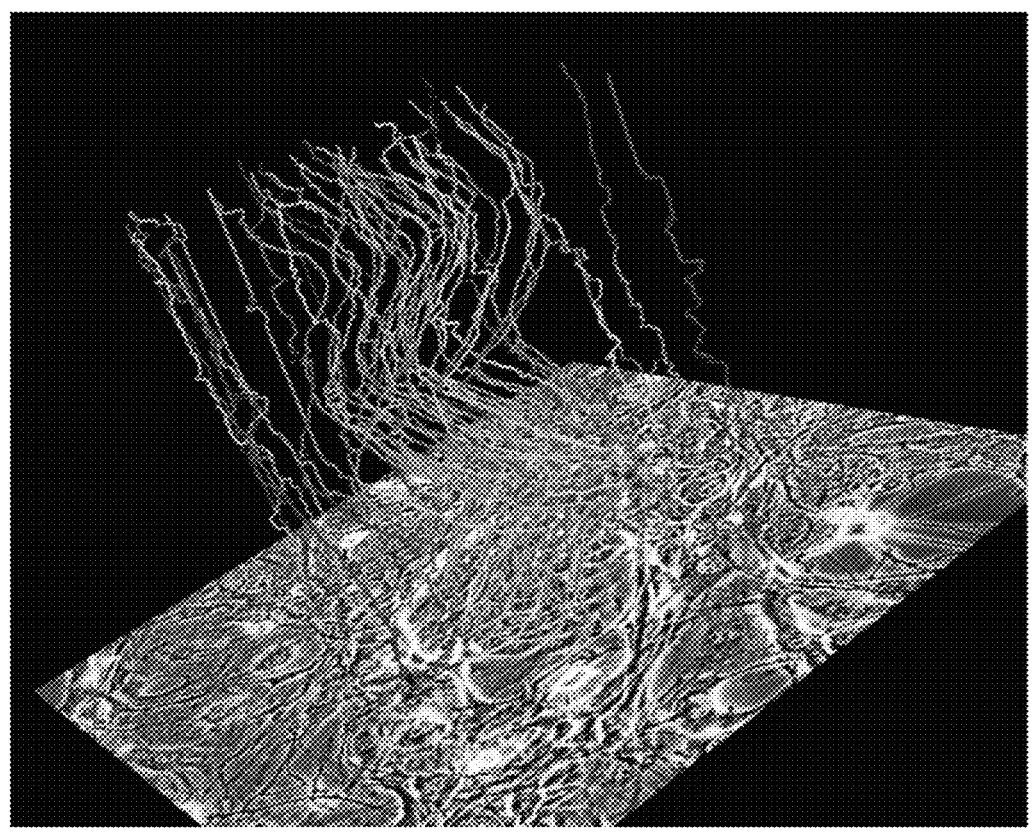
[Fig.11]
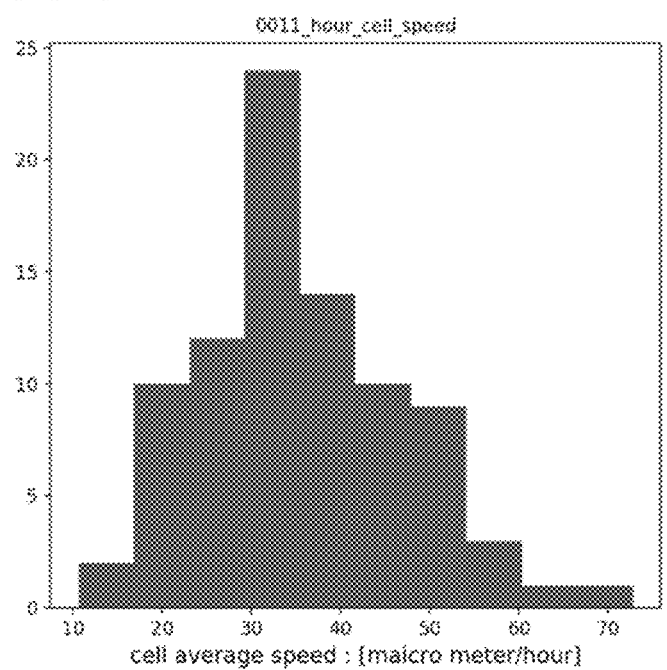

[Fig.12]
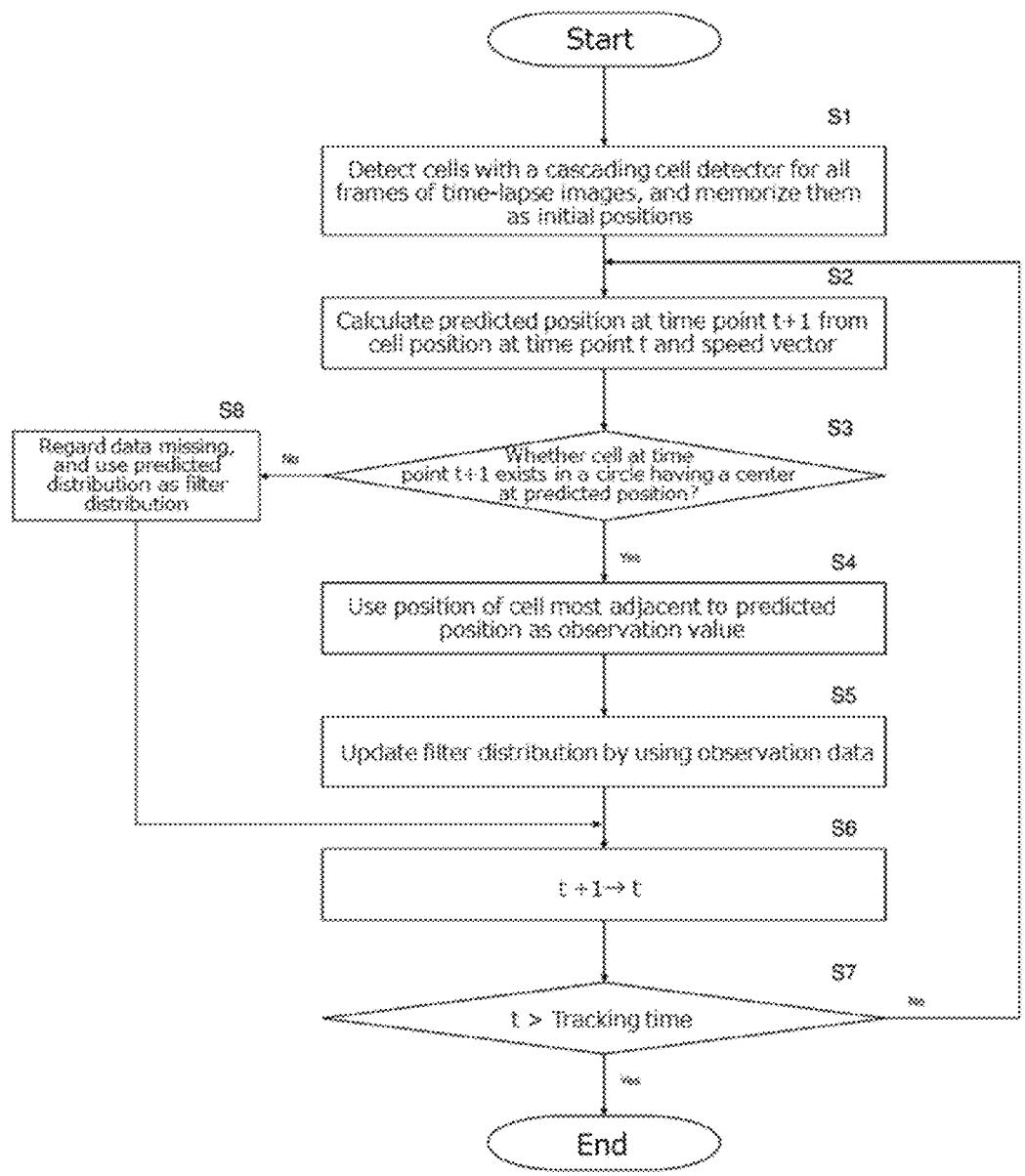

[Fig.13]
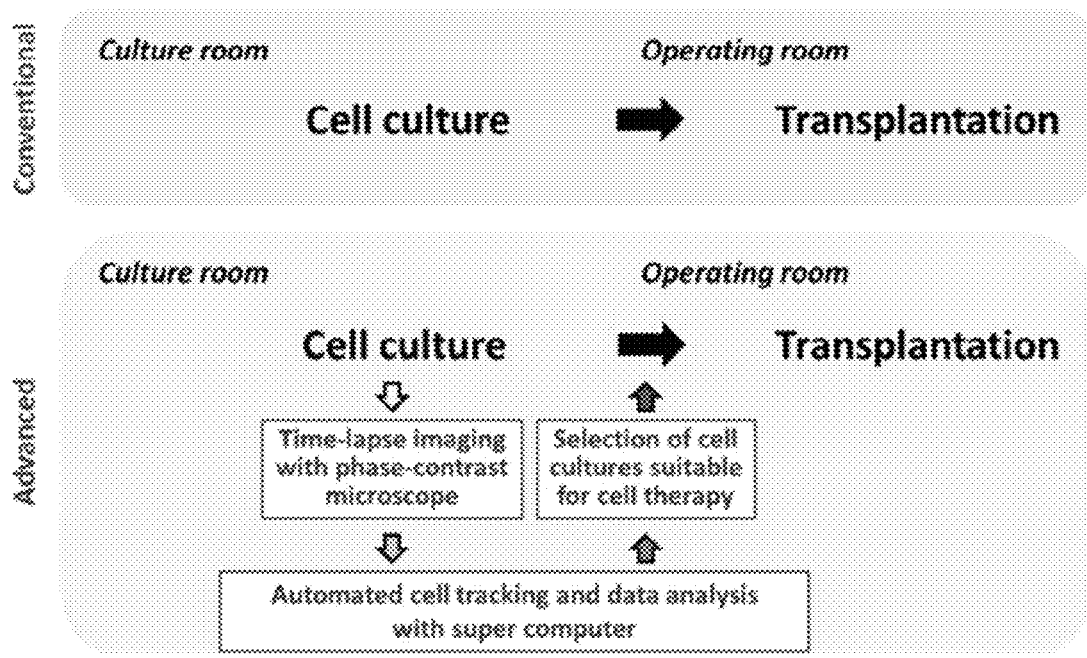

[Fig.14]
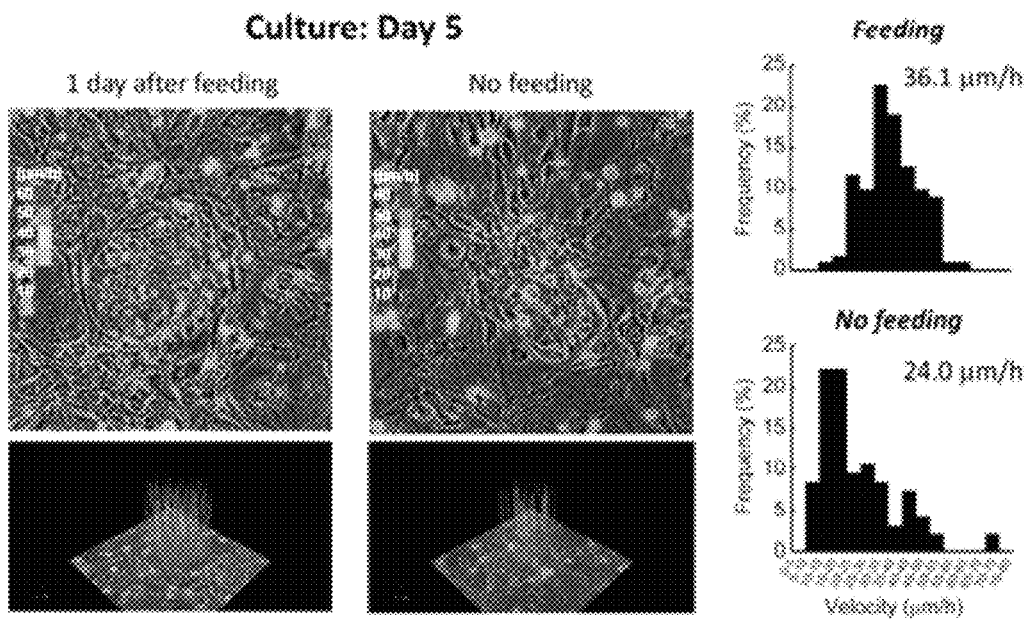
[Fig.15]
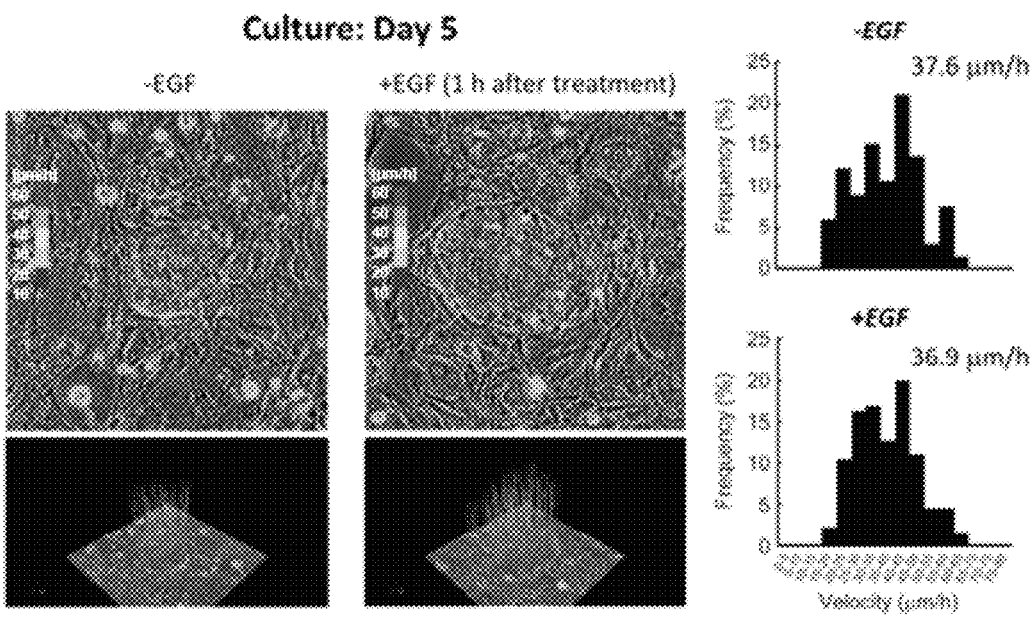

[Fig.16]
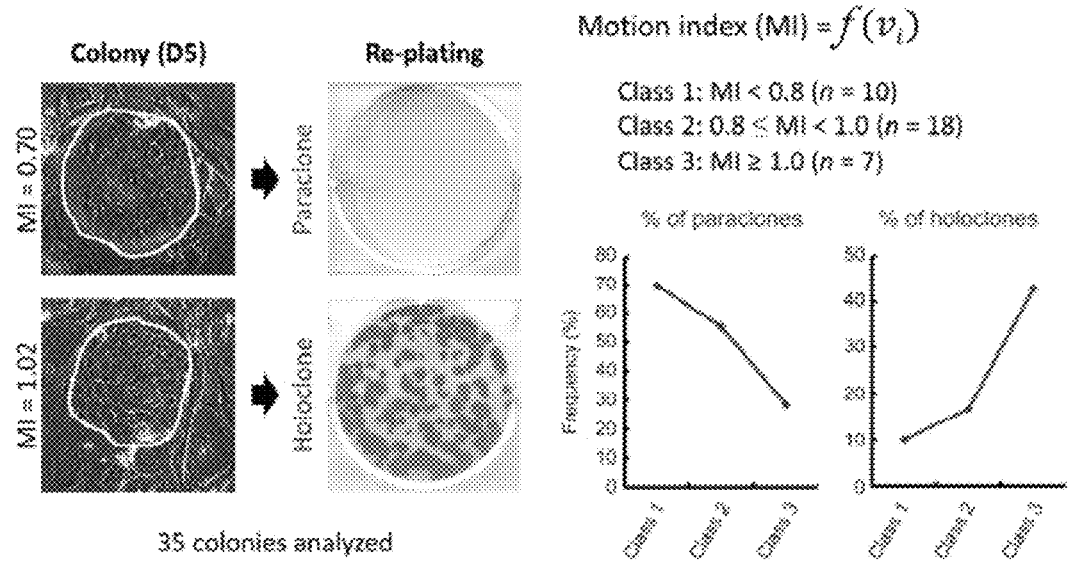
[Fig.17]
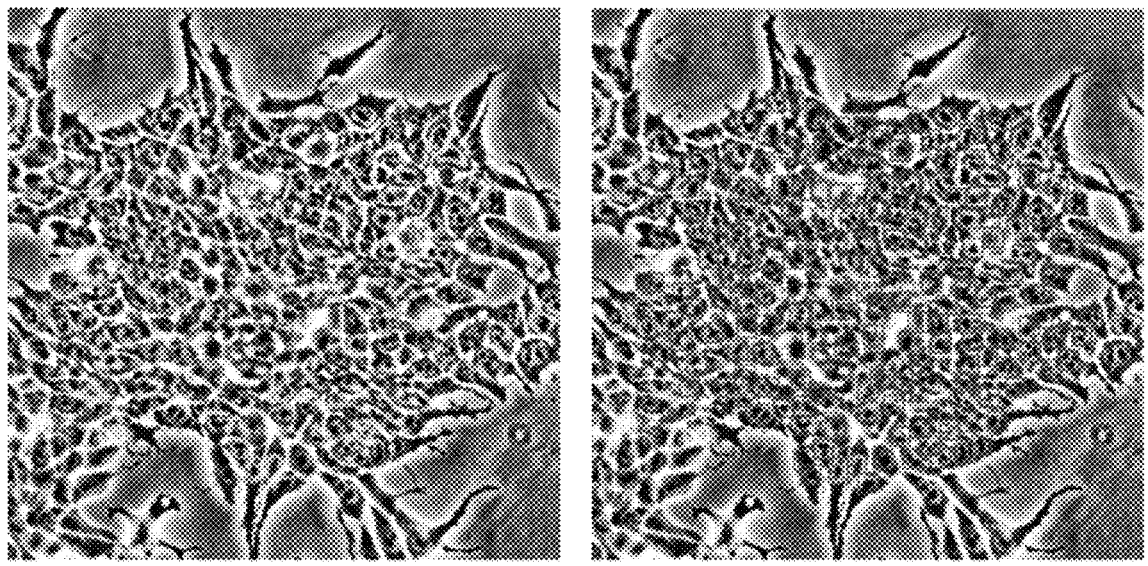

[Fig.18]
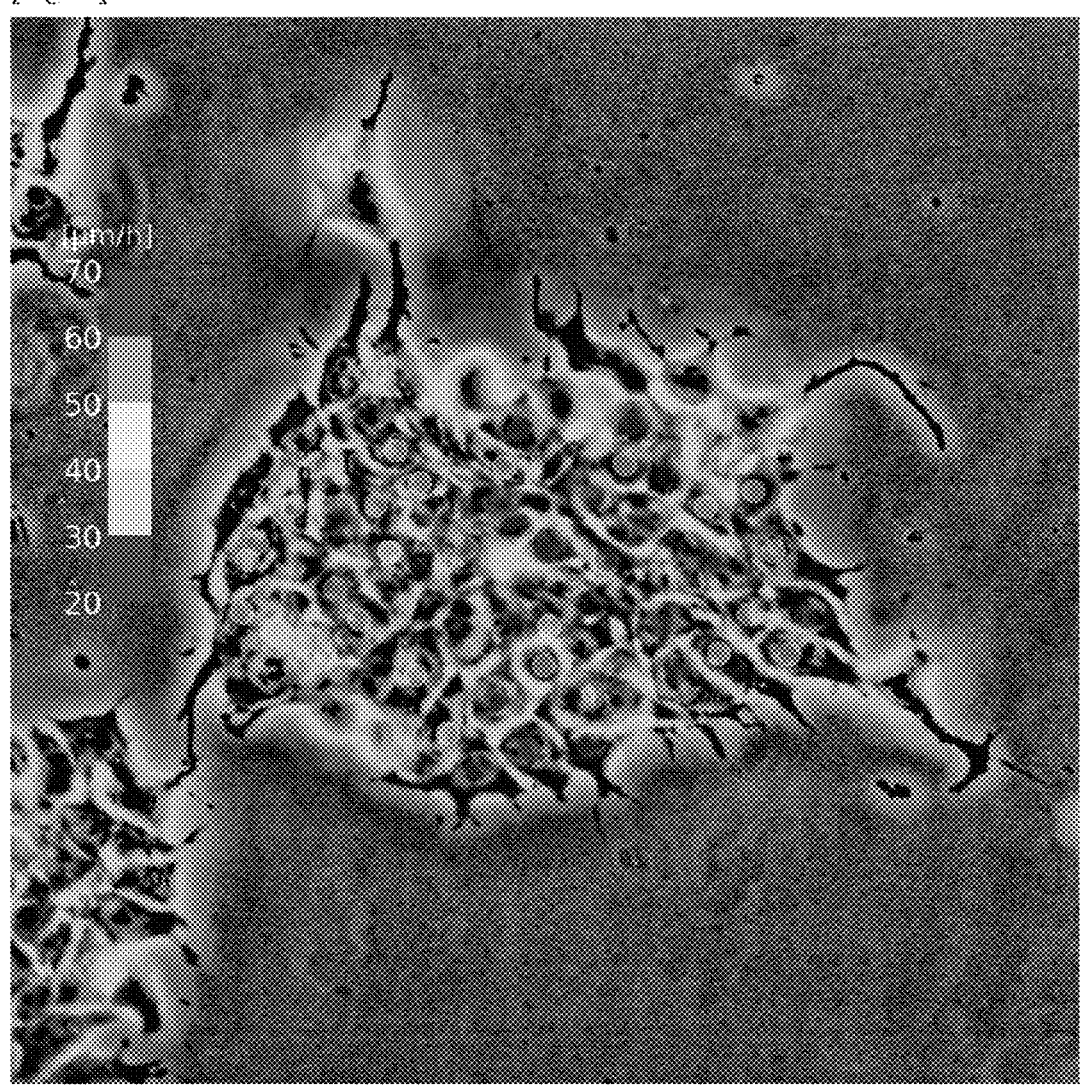

[Fig.19]
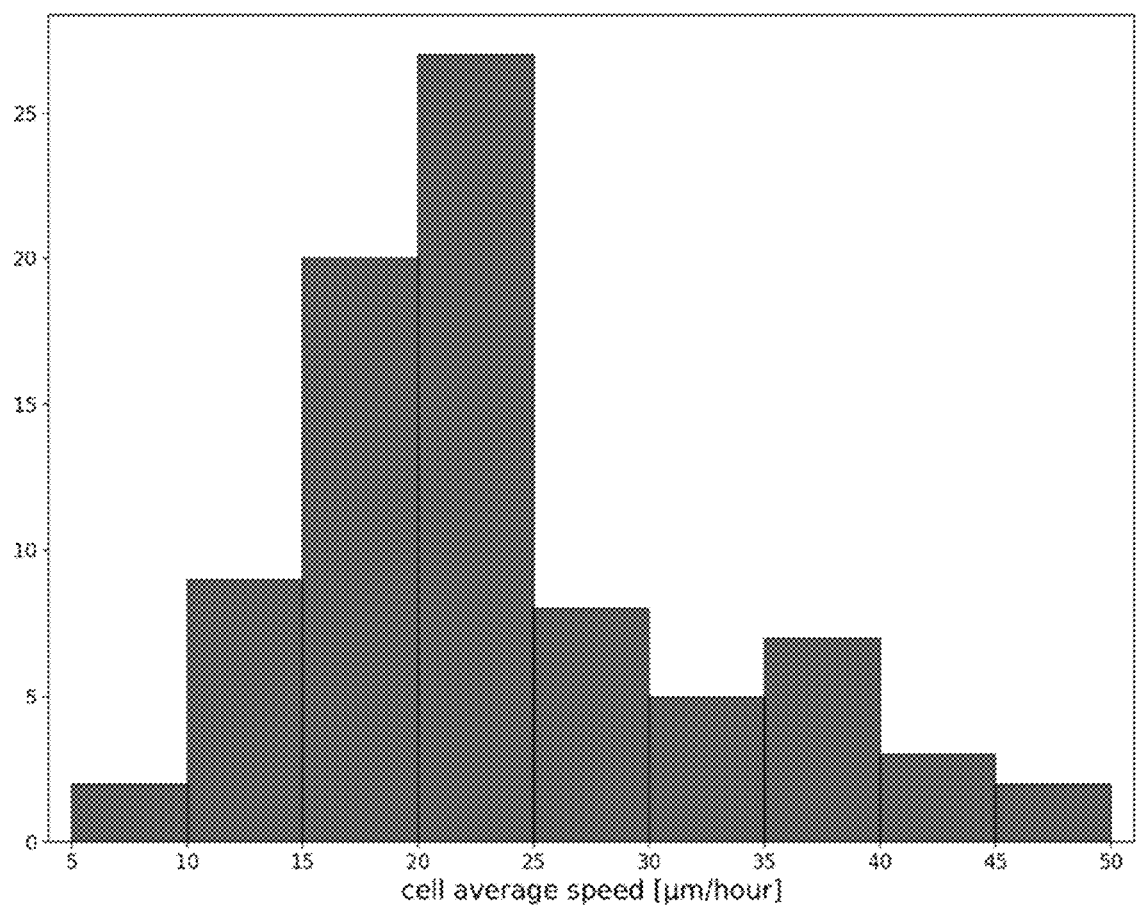

METHOD FOR ANALYZING BEHAVIOR OF CELL, AND USE THEREOF

TECHNICAL FIELD

The present invention relates to a method for analyzing behavior of a cell. More precisely, the present invention relates to a method for tracking a plurality of cells simultaneously, and automatically measuring locomotion speed of each cell. The method of the present invention can be used for evaluating quality of a stem cell, and is useful in the fields of, for example, regeneration medicine, and so forth.

BACKGROUND ART

There are being developed cultured epidermis transplantation techniques, in which epidermal keratinocytes having high proliferative capacity are obtained from a normal skin, and a sheet-shaped cultured epidermis is prepared by culture, and transplanted to a patient's skin injury part. For culture systems of human epidermal keratinocytes used for regeneration medicine, evaluation of culture conditions and content of cells having high proliferative capacity is important. Further, for epidermal cultured for the purpose of transplantation, quality control is required as products, unlike the cases of organ transplantation as medical practice.

Human epidermal keratinocytes easily lose proliferative capacity as a result of conditional change during cultivation. A large part of the cultivation and preparation of the sheet depends on highly skilled engineers, and this constitutes a serious obstacle of industrialization thereof. In order that a transplanted epidermal sheet engrafts and functions for a long period of time, it must contain keratinocyte stem cells, and identification thereof is not easy.

On the other hand, there have been examined methods for tracking kinetics of cells under culture on the basis of images taken at certain time intervals, and analyzing behaviors thereof, and automated systems therefor, and various examinations have been carried out in consideration of situations peculiar to cultured cells.

For example, in order to solve the problem of increase of a possibility for automatic tracking results obtained by such systems to include error data caused by adhesion of cells to one another under a high cell density condition, which makes cell boundaries ambiguous, Patent document 1 proposes, as an apparatus enabling automatic tracking of individual cells with high precision with non-invasive images even under a high cell density condition, a cell behavior analysis apparatus comprising a cell candidate region detection means that detects cell candidate regions of individual cells in time-lapse images for every frame of the time-lapse images so that many over-detections may be included, but almost no un-detection should be included, a hypothesis extraction means that extracts, for time-serially continuing two of the frames, a hypothesis for matching a cell region of a preceding frame, and the cell candidate region of a frame as an object of detection, a likelihood calculation means that calculates likelihood of the hypothesis extracted by the hypothesis extraction means, a hypothesis specification means that specifies an optimal hypothesis on the basis of the likelihood calculated by the likelihood calculating means, a cell region specification means that specifies cell candidate regions included in the hypothesis specified by the hypothesis specification means as the cell regions, and a memory means that memorizes tracking result data in which cell region information including positional information of the cell regions specified by the cell region specification means are stored in the order of time series.

Patent document 2 proposes, as a cell management system that enables easy grasping of conditions of cells at various time points, a cell management system comprising an acquisition means that acquires a plurality of data of object images obtained by imaging an objective cell population as a cell population constituted by a plurality of cells as evaluation objects in time series at a first time point as object image data, and acquires a plurality of image data of the objective cell population or an objective cell population derived from the objective cell population in time series at a second time point different from the first time point, a detection means that specifies each of a plurality of cells belonging to the objective cell population imaged by performing a predetermined image analysis for the plurality of object image data at the time points for every time point, and analyzes each of the specified cells in time series to detect behavior of each cell, a calculation means that calculates a cell behavior index that shows behavior index of a cell in the objective cell population at each time point on the basis of the behavior of each cell of the detected each objective cell population for every time point, a comparison means that performs a predetermined operation for comparing the calculated cell behavior indexes for the objective cell population at each time point, and a reporting means that reports at least one of calculation result calculated by the predetermined operation, and a predetermined information based on the calculation result.

Patent document 3 proposes, as a system for analyzing culture state of a culture liquid, which enables accurate non-invasive estimation of target items concerning cell culture such as particle size distributions and particle numbers of cell aggregates in a culture liquid, and as a result, accurate quality control or production control at low cost, a system for analyzing culture state of a culture liquid characterized by comprising a registration means that preliminarily registers, for each of a plurality of samples consisting of culture liquid containing cell aggregates, of which target items concerning culture are known and different, information including values of the target items and characteristic amount of the cell aggregates in an imaged specific region as a partial region of a container containing the culture liquid on a recording means as basic information, an acquisition means that acquires an objective image in which inside of the container containing the culture liquid as an estimation object is imaged from an imaging apparatus as object image data, an extraction means that performs a predetermined image analysis for an object image of the acquired object image data, and extracts a particle matching a focusing point from a particle group constituted by a plurality of particles imaged in the objective image as a focusing point matching particle indicating a cell aggregate existing in a specific region of the estimation object, a detection means that performs a predetermined image analysis for the object image to detect the characteristic amount for the extracted focusing point matching particle, an estimation means that performs a predetermined operation on the basis of the characteristic amount of cell aggregate in each registered basic information and the characteristic amount for the detected focusing point matching particle as a cell aggregate to estimate mixing ratio of basic information included in the estimation object, and a calculation means that performs a predetermined operation on the basis of the estimated mixing ratio and a value of the target item contained in each registered basic information to calculate the objective item of the estimation object.

Non-patent document 1 reports a fully automated multiple target tracking system that can simultaneously track and analyze thousands of cells observed by using a time-lapse phase contrast microscope. This system utilizes a fast geometric active contour tracker, and it is reported that 86.9 to 92.5% of tracking accuracy had been achieved by this system for various cell populations. Non-patent document 2 concerns particle tracking important for analysis of intracellular dynamic processes, and various automatic calculation methods for tracking a large number of individual particles are introduced and compared.

The inventors of the present invention also proposed, on the basis of correlation of kinetics of cells in a colony of stem cells and sternness of the cells in the colony, a method for evaluating cells obtained from an object in a culture system, which comprises the step of evaluating proliferative cell-constituted colony forming ability by using locomotion speeds of a plurality of cells in a colony derived from the cells in the culture system as an index, and in which locomotion speeds of the plurality of cells can be the mean locomotion speed of the plurality of cells, and the mean locomotion speed of the plurality of cells can be replaced with a motion index, which is obtained by calculating absolute values of brightness differences of pixels in the colony from two of colony images obtained with an interval, and dividing the total of absolute values of brightness differences in the colony with an area of the colony (Non-patent document 3, Patent document 4). They further proposed, for the purpose of automatizing calculation of locomotion speeds of cells in a colony, a method for evaluating cells, which comprises an imaging step of obtaining images of cells, a region specifying step of forming images for analysis from the cell images taken in the imaging step, and a locomotion speed calculation step of comparing images for analysis formed on the basis of cell images obtained at different time points to calculate locomotion speed of the colony, and in which, in the region specifying step, each cell image is divided into a plurality of blocks, distribution of brightness values in each block is calculated, the brightness values of each block are binarized on the basis of the distribution of brightness values in each block to identify the colony region, and an image for analysis in which blocks of the cell image other than a block corresponding to the colony region constitute the background is formed, and in the locomotion speed calculation step, locomotion speeds and locomotion directions of cells corresponding to each block locating in the colony region are calculated on the basis of the images for analysis of the cell images taken at different time points (Patent document 5).

PRIOR ART REFERENCES

Patent Documents

Patent document 1: Japanese Patent Unexamined Publication (KOKAI) No. 2014-85950 (Japanese Patent No. 6090770)
Patent document 2: Japanese Patent Unexamined Publication (KOKAI) No. 2017-23055
Patent document 3: Japanese Patent Unexamined Publication (KOKAI) No. 2017-140006
Patent document 4: Japanese Patent Unexamined Publication (KOKAI) No. 2014-83042 (Japanese Patent No. 6218208)
Patent document 5: Japanese Patent Unexamined Publication (KOKAI) No. 2018-19632

Non-Patent Documents

Non-patent document 1: Med. Image Anal., 2008; 12(5): 546-66
Non-patent document 2: Nature Methods, 2014; 11:281-289
Non-patent document 3: J. Cell Biol., 2015; 209(2):305-15

SUMMARY OF THE INVENTION

Object to be Achieved by the Invention

Although it had already been found that locomotion speeds of cells correlate with stemness as described above, what is problem was that the measurement of the locomotion speed must be actually performed by human power, and thus the burden in the field is extremely heavy. Especially for forming a colony of densely aggregating cells such as human epidermal keratinocytes, highly precise automatic tracking of each cell and analysis of behavior of each cell at good precision had not been achieved by the existing automatic cell recognition techniques.

Further, the methods reported in Non-patent documents 1 and 2 cannot be used other than when contours of individual cells are clear such as when cells are in a comparatively loose state.

Means for Achieving the Object

Then, the inventors of the present invention conducted various researches for constructing a mathematical model enabling tracking of each single human epidermal keratinocyte, and automatic measurement of the speed thereof, and implementing it on a computer. And they tried use of a dictionary of correct answer images obtained from actual cells for detection of cells, use of a state space model using most adjacent cells as observation data for tracking, and so forth. As a result, they confirmed that locomotion speeds of a plurality of cells can be automatically calculated, and cells showing a high locomotion speed, i.e., cells showing high proliferative activity, can be automatically specified by such a method, and accomplished the present invention.

The present invention provides the followings.
[1] A method for analyzing behavior of a cell, the method comprising:
detecting positions of a plurality of cells for every frame of time-lapse images, while determining whether a candidate region extracted from the frame is a cell region by using a dictionary containing image data of cell nuclei; and
tracking each cell by using a state space model using position of a most adjacent cell within a predetermined distance from a predicted position as observation data.
[2] A method for evaluating a cell, the method comprising:
detecting positions of a plurality of cells for every frame of time-lapse images, while determining whether a candidate region extracted from the frame is a cell region by using a dictionary containing image data of cell nuclei;
tracking position of each cell by using a state space model using position of a most adjacent cell within a predetermined distance from a predicted position as observation data; and
calculating speed information of each cell on the basis of tracking information obtained in the tracking step.
[3] The method according to 1 or 2, wherein the tracking step uses a position of a forward most adjacent cell within a predetermined distance from a predicted position as the observation data.

[4] The method according to 3, wherein the determination is performed by using deep learning.

[5] The method according to any one of 1 to 4, wherein, in the tracking step, when any cell is not found within the predetermined distance from a predicted position, the data are considered missing.

[6] The method according to any one of 1 to 5, wherein the cell is a stem cell.

[7] The method according to 6, wherein interval of previous time and present time is 2 to 15 minutes.

[8] The method according to any one of 1 to 7, which is used for quality evaluation of a cultured tissue for cell therapy.

[9] A method for producing a cultured tissue, the method comprises:
culturing cells obtained from an object to prepare a cultured tissue for transplantation; and
evaluating the prepared cultured tissue by using locomotion information of cells contained in the cultured tissue as an index; and wherein the evaluation step comprises:
detecting positions of a plurality of cells for every frame of time-lapse images of all or a part of the cultured tissue;
tracking each cell by using a Kalman filter of which observation data is a position of a most adjacent cell within a predetermined distance from a predicted position of the cell at present time, which is the position of the cell in the frame of previous time point; and
calculating locomotion information of each cell on the basis of tracking information obtained in the tracking step.

[10] The method according to 9, wherein the cultured tissue is cultured epidermis, cultured corneal epithelium, or cultured cartilage.

[11] A cell behavior analysis apparatus comprising:
a detection means for detecting positions of a plurality of cells for every frame of time-lapse images, while determining whether a candidate region extracted from the frame is a cell region by using a dictionary containing image data of cell nuclei;
an estimation means for estimating position of each cell by using a state space model using position of a most adjacent cell within a predetermined distance from a predicted position as observation data; and
a memory means for memorizing the estimated position of each cell at each time point.

[12] A cell evaluation apparatus comprising:
a detection means for detecting positions of a plurality of cells for every frame of time-lapse images, while determining whether a candidate region extracted from the frame is a cell region by using a dictionary containing image data of cell nuclei;
an estimation means for estimating position of each cell by using a state space model using position of a most adjacent cell within a predetermined distance from a predicted position as observation data;
a memory means for memorizing the estimated position of each cell at each time point; and
a calculation means for calculating locomotion information of each cell on the basis of the estimated position at each time point memorized in the memory means.

[13] A program for cell behavior analysis, the program being for making a computer execute:
detecting positions of a plurality of cells for every frame of time-lapse images, while determining whether a candidate region extracted from the frame is a cell region by using a dictionary containing image data of cell nuclei; and
tracking each cell by using a state space model using position of a most adjacent cell within a predetermined distance from a predicted position as observation data.

[14] A program for evaluation of a cell, the program being for making a computer execute:
detecting positions of a plurality of cells for every frame of time-lapse images, while determining whether a candidate region extracted from the frame is a cell region by using a dictionary containing image data of cell nuclei;
tracking position of each cell by using a state space model using position of a most adjacent cell within a predetermined distance from a predicted position as observation data; and
calculating locomotion speed and locomotion direction of each cell on the basis of position information obtained in the tracking step.

[15] A system for providing a cultured tissue for an object, the system comprising:
culturing collected cells to produce a cultured tissue;
performing quality evaluation of a cell tissue under culture or the produced cultured tissue;
choosing a cultured tissue on the basis of result of the quality evaluation; and
providing the chosen quality-evaluated cultured tissue for the object.

The present invention also provides the followings.

[1] A method for analyzing behavior of a cell, the method comprising:
detecting positions of a plurality of cells for every frame of time-lapse images; and
tracking each cell by using a state space model using position of a most adjacent cell within a predetermined distance from a predicted position as observation data.

[2] A method for evaluating a cell, the method comprising:
detecting positions of a plurality of cells for every frame of time-lapse images;
tracking position of each cell by using a state space model using position of a most adjacent cell within a predetermined distance from a predicted position as observation data; and
calculating speed information of each cell on the basis of tracking information obtained in the tracking step.

[3] The method according to 1 or 2, wherein the detection step comprises determining whether a candidate region extracted from the frame is a cell region by using a dictionary.

[4] The method according to 3, wherein the determination is performed by using deep learning.

[5] The method according to 3 or 4, wherein the dictionary contains image data of cell nuclei.

[6] The method according to any one of 1 to 5, wherein, in the tracking step, when any cell is not found within the predetermined distance from a predicted position, the data are considered missing.

[7] The method according to any one of 1 to 6, wherein the cell is a stem cell.

[8] The method according to 7, wherein interval of previous time and present time is 2 to 15 minutes.

[9] A method for producing a cultured tissue, the method comprising:
culturing cells obtained from an object to prepare a cultured tissue for transplantation; and
evaluating the prepared cultured tissue by using locomotion information of the cells contained in the cultured tissue as an index; and wherein the evaluation step comprises:
detecting positions of a plurality of cells for every frame of time-lapse images of all or a part of the cultured tissue;
tracking each cell by using a state space model using position of a most adjacent cell within a predetermined distance from a predicted position of the cell at present time, which is the position of the cell in the frame of previous time point, as observation data; and calculating locomotion information of each cell on the basis of tracking information obtained in the tracking step.

[10] The method according to 9, wherein the cultured tissue is cultured epidermis, cultured corneal epithelium, or cultured cartilage.

[11] A cell behavior analysis apparatus comprising:
a detection means for detecting positions of a plurality of cells for every frame of time-lapse images;
an estimation means for estimating position of each cell by using a state space model using position of a most adjacent cell within a predetermined distance from a predicted position as observation data; and
a memory means for memorizing the estimated position of each cell at each time point.

[12] A cell evaluation apparatus comprising:
a detection means for detecting positions of a plurality of cells for every frame of time-lapse images;
an estimation means for estimating position of each cell by using a state space model using position of a most adjacent cell within a predetermined distance from a predicted position as observation data;
a memory means for memorizing the estimated position of each cell at each time point; and
a calculation means for calculating locomotion information of each cell on the basis of the estimated position at each time point memorized in the memory means.

[13] A program for cell behavior analysis, the program being for making a computer execute:
detecting positions of a plurality of cells for every frame of time-lapse images; and
tracking each cell by using a state space model using position of a most adjacent cell within a predetermined distance from a predicted position as observation data.

[14] A program for evaluation of a cell, the program being for making a computer execute:
detecting positions of a plurality of cells for every frame of time-lapse images;
tracking position of each cell by using a state space model using position of a most adjacent cell within a predetermined distance from a predicted position as observation data; and
calculating locomotion speed and locomotion direction of each cell on the basis of position information obtained in the tracking step.

Effect of the Invention

By continuously monitoring cells to obtain speed vector for every cell, especially changes of culture conditions to undernutrition condition, low temperature condition, etc. can be immediately perceived without people staying at the spot. Epidermal keratinocytes showing extremely reduced proliferative capacity due to improper culture can also be detected. Conversely, it also becomes possible to detect keratinocytes suitable for transplantation by identifying keratinocyte stem cells. This method can further be applied to other cell species, can be a fundamental technique for regeneration medicine using cells, and enables quality control including optimization of culture conditions and non-invasive identification of epidermis keratinocyte stem cells during culture.

By using data showing nucleus morphology of cells, behavior of each cell can be analyzed even for cell populations in which borders of cells are not clear.

BRIEF DESCRIPTION OF THE DRAWINGS

FIG. 1 Examples of cell dictionary. A dictionary in which cell nucleus is enclosed with a rectangle (left), and a dictionary in which what is not cell nucleus is enclosed with a rectangle (right).

FIG. 2 Dictionary images of cell nuclei at the mitotic phase.

FIG. 3-1 Conceptual diagrams of three kinds of deep convolution networks (DCN1, DCN2, and DCN3).

FIG. 3-2 A model conceptual diagram of SSD. SSD is a material detection algorithm with a network structure in which multiple convolution layers are stacked.

FIG. 3-3 Conceptual diagrams of two kinds of capsule networks (CapsNet1 and CapsNet2).

FIG. 4-1 A conceptual diagram of the determination apparatus used for the cell determination described herein.

FIG. 4-2 A conceptual diagram of a cascading cell detector. The cascading cell detector comprises a structure consisting of SSD and CapsNet shown in FIGS. 3-2 and 3-3, respectively, which are stacked in multiple stages.

FIG. 5-1 Examples of detection of positions of cells. Extraction of candidate region at the first stage (left), and determination of cell region (right). The candidate region is a region indicated in the rectangle. The rectangle in the right photograph indicates the region determined in the second stage.

FIG. 5-2 A diagram showing regions to be inputted into SSD. There are shown an example in which the image is divided into 16 portions in a size of 256×256, and an example in which the image is divided into 9 portions in a size of 341×341. By dividing the image into two kinds of sizes, the detection was performed so that there should not be any overlooked region.

FIG. 6 A detection flowchart for a cascading cell detector. The numbers indicated on the side of the arrows are numbers of candidate regions that advanced to the step indicated with the allows for a certain microscopic image.

FIG. 7 An example of cell tracking. Predicted positions of cells at time point t (white dots), and positions of the cells at time point t (stars). The circles are such circles that the positions of the most adjacent stars included in the circles are the observation data. In this example, the data were observed in the lower circle, but missed in the upper circle.

FIG. 8 An example of cell tracking. The image is constituted by overlapping tracking regions of continuous time points for focused one cell. The line was drawn by connecting the centers of the regions, and represents trajectory of the cell.

FIG. 9 An example of cell tracking.

FIG. 10 An example of space-time diagram of cells. In the diagram, trajectories of the cells are drawn, in which the vertical axis indicates the direction of time.

FIG. 11 An example of speed histogram.

FIG. 12 A flowchart showing flow of one embodiment of the cell behavior analysis.

FIG. 13 An example of novel system for cell therapy.

FIG. 14 An example of monitoring of culture conditions.

FIG. 15 An example of monitoring of culture conditions.

FIG. 16 An example of evaluation of stemness.

FIG. 17 Examples of detection result of ES cells.

FIG. 18 An example of tracking of ES cells.

FIG. 19 An example of speed histogram of ES cells.

MODES FOR CARRYING OUT THE INVENTION

The cell behavior analysis method of the present invention will be explained with reference to FIGS. 1 to 12.

[Detection Step]

In this step, a cell candidate region is extracted from each frame (each time point) of time-lapse images of a cell population including a plurality of cells (for example, one colony) obtained with a constant time interval, and it is determined whether each region is a cell region or not to determine positions of the plurality of cells. The role of the detection step is decision of the initial position of the cell tracking for a plurality of cells, and generation of observation data in a state space model for every time point. Typically, in the detection step, the determination is performed for all the images of the time-lapse images by using a cascade type distinction apparatus to detect the cells, and the initial positions and the positions of the cells at each time point are determined, and memorized (FIG. 12, S2).

Although the interval of the time-lapse imaging can be appropriately determined depending on the type of the objective cell, when it is intended to evaluate quality of cells by using locomotion speed of the cells as an index as described later, it is preferably performed for cells under usual culture conditions (for example, 37° C. and 5 to 10% $CO_2$), and the interval can be determined in consideration of the locomotion speed of the cells. Since the locomotion speed of cell is usually low, and is several to several tens μm/h, it is appropriate to perform the imaging with an interval of 1 minute or longer, and in order to properly perform the tracking according to the method of the present invention, imaging is preferably performed for every time period shorter than that required for cells to move a distance corresponding to the size of one cell (for example, 6 to 20 μm in the case of mammalian cell) (for example, every 2 to 15 minutes, preferably every 1 to 10 minutes, more specifically, every 3 to 7 minutes).

Cell image processing may be performed for the time-lapse images. The cell image processing is an image processing performed in order to make the structure of cell conspicuous, and it is, for example, the histogram data smoothing, or the like.

<Dictionary Creation>

For the extraction of cell candidate region and determination of whether the region is a cell region, a data set (dictionary) is used. The dictionary is collection of image data generated from all the regions recognized as each cell or characteristic parts of them from images taken in an actual culture system. When the cells as the target of the analysis are eucaryocytes, the regions chosen for the above purpose are preferably created from parts of cell nuclei, which show comparatively less differences in size and morphology depending on the type of the cells, in consideration of possible indefinite outer edges of cells at the time of the analysis of behavior of a plurality of cells, which is caused by adhesion of the cells, and so forth. FIG. 1 shows a phase contrast microscopic image in which portions recognized to be cell nuclei with the human naked eye are enclosed with rectangles (left), and a phase contrast microscopic image in which portions recognized not to be cell nuclei are enclosed with rectangles (right).

The dictionary may include, in addition to the actually taken images (original images), images obtained by subjecting the original images to an extension processing. The extension processing may be performed by, for example, flip vertical, flip horizontal, gamma correction, change of resolution, rotation, or a combination of these. Extension of the dictionary data may be performed in each stage of the deep learning described later.

The dictionary of cell nuclei may be constituted so as to include images of cell nuclei at a specific stage of the cell cycle. When cells showing high proliferative capacity such as stem cells are used as the object, such constitution of the dictionary as mentioned above is preferred. The cell cycle is divided into the interphase and M phase, and the interphase is further divided into the $G_1$ phase, S phase, and $G_2$ phase. The M phase may also be referred to as mitotic phase. FIG. 2 shows examples of the dictionary image of nucleus of cell at the mitotic phase.

When a dictionary generated from images of cell nucleus portions is used for the present invention, the cell may mean cell nucleus. When a dictionary of cell nuclei is used, the candidate region of cell means a candidate region of cell nucleus, and the cell region means region of cell nucleus.

<Learning for Cell Detection>

In order to extract candidate regions of cells from each time-lapse image, a model of deep learning can be used as an algorithm for material detection. Specifically, a model of deep learning called SSD proposed recently (refer to the reference [2] in the list mentioned in the last part of this specification) can be used (first stage SSD). Data extension of the dictionary may be performed at the time of this learning.

The candidate regions extracted in the first stage SSD may actually include many regions that are not cells. Therefore, in order to distinguish cell regions among these candidate regions with high precision, a deep convolution network based on VGG16 (refer to the reference [3]), which is classified into class 2, can be used. Data extension of dictionary may be performed at the time of this learning. The conceptual diagrams of three kinds of convolution networks (DCN1, DCN2, and DCN3) are shown in FIG. 3. A cascading network consisting of these models combined in multiple stages is shown in FIG. 4.

The specific flow will be explained with reference to FIG. 4. One colony image (cell colony image) is first inputted, and a plurality of candidate regions (cell candidates) are picked up from the image by SSD. Each of the images of the candidate regions is distinguished with DCN1, and those determined to be cell are grouped as a cell group (Cell #1). The images that have not been judged to be a cell by DCN1 are distinguished with DCN2. Those determined to be a cell with DCN2 are grouped as a cell group (Cell boxes). Those still judged not to be a cell with DCN2 are further distinguished with DCN3. Those determined to be a cell are grouped as a cell group. Those still judged not to be a cell with DCN3 are regarded not to be a cell (cell region negative).

Three kinds of the convolution networks (DCN1, DCN2, and DCN3) can learn independently. At the time of this learning, data extension of the dictionary image may be performed. Adam (reference [4]) may be used as the optimization algorithm, and Chainer (reference [5]) may be used for the construction of the cascading network.

[Tracking Step]

In this step, tracking is performed for each of a plurality of cells detected in the detection step. A state space model can be used for the tracking. Specifically, from cell position (position of the center of the rectangle surrounding the nucleus of the detected cell) at the time point t (frame of time point t) and a speed vector, the predicted position at the time point t+1 is calculated (FIG. 12, S2). Such calculation of predicted position is performed for each of the plurality of cells. The term predicted position used in the present invention refers to a predicted position predicted by a state space model. The predicted position is obtained by adding the speed at the previous time point and a fixed random number as turbulence to the position of the cell at the previous time.

More specifically, a linear state space model described by the observation equation and state equation shown below can be used as an algorithm for tracking each one single cell.

$$z_t = Hx_t + v_t \quad \text{[Equation 1]}$$

$$x_t = Fx_{t-1} + w_t$$

$$x_t = \begin{bmatrix} x_t \\ y_t \\ u_t \\ v_t \end{bmatrix}, F = \begin{bmatrix} 1 & 0 & 1 & 0 \\ 0 & 1 & 0 & 1 \\ 0 & 0 & 1 & 0 \\ 0 & 0 & 0 & 1 \end{bmatrix},$$

$$z_t = \begin{bmatrix} z_{x,t} \\ z_{y,t} \\ z_{u,t} \\ z_{v,t} \end{bmatrix}, H = \begin{bmatrix} 1 & 0 & 0 & 0 \\ 0 & 1 & 0 & 0 \\ 0 & 0 & 1 & 0 \\ 0 & 0 & 0 & 1 \end{bmatrix}$$

In the equations, $x_t$ represents a state vector, $(x_t, y_t)$ represents coordinate of a cell at a time point t, and $(u_t, v_t)$ represents a speed vector of the cell at the time point t. F is a transition matrix, and H is an observation matrix. $z_t$ is an output vector corresponding to $x_t$. $v_t$ and $w_t$ represent a Gaussian white noise vector. This linear state space model is updated by using a Kalman filter.

Observation data can be generated as follows. It is determined whether a cell exists in a circle of a predetermined radius having a center at a predicted position (FIG. 12, S2). When cells exist, coordinate of the cell nearest to the predicted position is used as observation data. When any cell does not exist in the circle, it is considered that data are missing (FIG. 12, S8).

In the following diagram, the cell enclosed in □ provides observation data at a time point t+1.

[Equation 2]

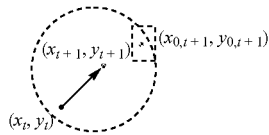

FIG. 7 shows examples of determination of observation cell and data missing at contiguous two time points. The lower circle indicates an example of the case that position of a cell is found in the observation range of the predicted position at a certain time point.

By using the cell position in this circle as observation data (FIG. 12, S4), filter distribution of Kalman filter is updated (FIG. 12, S5).

On the other hand, the upper circle shown in FIG. 7 indicates an example of the case where coordinate is not found in the observation range, and in this case, data are considered missing (FIG. 12, S8), and the process advances to the following time step without performing the filtering.

Although the size of the circle can be appropriately set depending on the objective cell, or according to the interval of the time-lapse imaging, when it is intended to evaluate the quality of cells by using locomotion speed of the cells as an index as described later, the interval of the time-lapse imaging can be set to be about 3 to 7 minutes, and then the size of the circle can be set to be 0.5 to 1.5 times the size of cell (for example, 6 to 20 μm in the case of mammalian cell).

Alternatively, for a method constructed for tracking every single cell by using a general state space model, the following model can be proposed.

$$x_t = f_t(x_{t-1}) + \omega_t$$

$$z_t = h_t(x_t) + v_t \quad \text{[Equation 3]}$$

In the equations, $x_t$ represents a speed vector:

$$x_t = \begin{pmatrix} x_t \\ y_t \\ v_{x,t} \\ v_{y,t} \\ a_{x,t} \\ a_{y,t} \end{pmatrix} \quad \text{[Equation 4]}$$

wherein $(x_t, y_t)$ represents coordinate of a cell at a time point t, $(v_{x,t}, v_{y,t})$ represents a speed vector of the cell at the time point t, and $(a_{x,t}, a_{y,t})$ represents acceleration of the cell at the time point t. $z_t$ is an output vector corresponding to $x_t$. $v_t$ and $w_t$ represent a noise component. This general state space model is updated by using an ensemble Kalman filter.

A conceptual diagram of the tracking using an ensemble Kalman filter is shown in FIG. 8. In the data generation in the case of this tracking, coordinate of a most adjacent cell within a distance of a radius of 20 pixels from the predicted coordinate is first set to be a candidate coordinate of observation value, and when a cell does not exist within the distance of a radius of 20 pixels, data are considered missing. Then, a unit vector of the speed vector at the candidate coordinate of observation, $$\frac{v_c}{\|v_c\|}, \quad \text{[Equation 5]}$$

and a unit vector of the speed vector of the predicted value $$\frac{v_p}{\|v_p\|} \quad \text{[Equation 6]}$$

are multiplied to calculate an inner product thereof, $$\left( \frac{v_p}{\|v_p\|}, \frac{v_c}{\|v_c\|} \right), \quad \text{[Equation 7]}$$

and when it satisfies the condition $$0 < \left( \frac{v_p}{\|v_p\|}, \frac{v_c}{\|v_c\|} \right) < 1, \quad \text{[Equation 8]}$$

this candidate value is used as the observation value in the tracking.

[Equation 9]

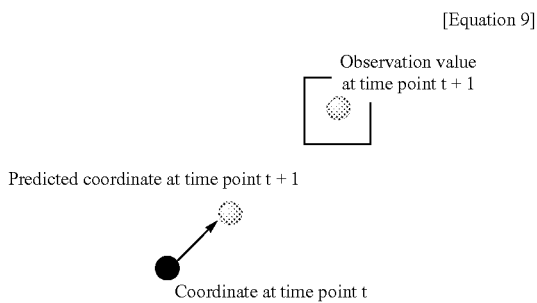

The cell enclosed in the rectangle serves as an observation cell at the time point t+1. When any recognized cell is not observed within the range of radius of 20 pixels, data are regarded missing.

In the tracking step, position of a most adjacent cell within a range of a predetermined distance from a predicted position is used as observation data. At this time, it is preferred that position of the most adjacent forward cell with respect to the cell at the time point t among cells locating within the predetermined distance from the predicted position is used as the observation data. The forward cell refers to a cell of which inner product of the unit speed vector and unit predicted position vector is represented as a positive value. When there are a plurality of such cells, a cell having an inner product nearest to 1 can be chosen.

FIG. 8 shows an example of independently tracking each single cell according to such a principle as mentioned above. FIG. 9 shows an example of tracking each of a plurality of cells. FIG. 10 shows an example of plotting of trajectory of each cell as a three-dimensional trajectory using the time axis in the height direction.

[Calculation Step and Evaluation Step]

In the calculation step, speed information of each cell (speed vector, locomotion speed, locomotion direction, etc.) is calculated on the basis of the tracking information obtained in the tracking step. If norms of the obtained speed vectors at all the time points are added and divided with the time, average locomotion speed of the cell can be obtained. A cell population can be evaluated by calculating average locomotion speed for each of the plurality of cells, and creating a histogram. An example of such a histogram is shown in FIG. 11.

[Apparatus and Program]

The present invention also provides a cell behavior analysis apparatus for implementing the aforementioned cell behavior analysis method, and a cell evaluation apparatus for implementing the aforementioned cell evaluation method.

Specifically, the cell behavior analysis apparatus comprises a cell detection means that detects positions of a plurality of cells for every frame of time-lapse images; an estimation means that estimates position of each cell by using a state space model using position of a most adjacent cell within a predetermined distance from a predicted position as observation data; and a memory means that memorizes estimated position of each cell at each time point. The cell evaluation apparatus further comprises a calculation means that calculates locomotion information of each cell on the basis of the estimated position at each time point memorized in the memory means.

The functions of the cell behavior analysis apparatus and cell evaluation apparatus mentioned above may be realized by a computer. In such a case, a program for realizing the functions may be recorded on a computer-readable recording medium, read and executed by a computer system to realize the functions. The "computer system" referred to here includes OS and hardware including peripheral equipments. The "computer-readable recording medium" means a memory, for example, portable media such as flexible disk, magnetic optical disk, ROM, and CD-ROM, hard disk built in a computer system, and so forth. The "computer-readable recording medium" may further be one that can dynamically retain a program for a short period of time like networks such as the internet, or a communication line such as telephone line in the case of transmitting a program via communication lines, or one that retains a program for a certain period of time such as volatile memory built in a computer system used as a server or client in such a case as mentioned above. The aforementioned program may also be one for realizing a part of the functions mentioned above, or may be one that can realize the functions mentioned above in combination with a program already recorded on the computer system.

[Use of Cell Behavior Analysis Method]

<Cell>

The method of the present invention can be used for various kinds of cells. It can be preferably applied to eucaryocytes, and can be particularly preferably applied especially to a cell population including stem cells. The stem cell referred to in the present invention is a cell having a self-replication ability and an ability to differentiate into a plurality of kinds of cell lineages, unless especially indicated. The stem cell referred to in the present invention includes epidermis keratinocyte stem cell, skin stem cell, retinal stem cell, retinal epithelial stem cell, cartilage stem cell, hair-follicle stem cell, muscle stem cell, bone precursor cell, fat precursor cell, hematopoietic stem cell, neural stem cell, liver stem cell, pancreas stem cell, ectodermal stem cell, mesodermal stem cell, endodermal stem cell, mesenchymal stem cell, ES cell (embryonic stem cell), and iPS cell, as well as stratified squamous epithelial cell (including tumor cells) and induced epidermal keratinocyte stem cell.

<Quality Evaluation of Cultured Tissue>

The method of the present invention can be used for evaluating a cell obtained from an object for proliferative capacity in a culture system by using locomotion speed of the cell as an index. The inventors of the present invention found that, in a cultured human epidermal keratinocyte culture system, the average locomotion speed of the cells is maximized in a colony constituted by cells of high proliferative capacity, especially a colony constituted by keratinocyte stem cells, and also found that the proliferative capacity of human epidermal keratinocyte correlates with locomotion speed thereof (Non-patent document 1, Patent document 4). Any method for non-invasively and automatically evaluating culture conditions and cultured cells have not existed so far to date. However, according to the present invention, in which cells are evaluated on the basis of behavior analysis of a group of cells, automated noninvasive evaluation can be attained. Further, conventional management of the culture conditions for maintaining proliferative capacity of stem cells etc. depend on engineers' experiential knowledge. In the field of regeneration medicine, quality control is required for cells cultured for the purpose of transplantation as medical products. Cells for preparing a cultured tissue for transplantation probably usually differ depending on individuals from whom the cells have been derived, and thus completed cell products may have various variations. While quality control of cultured tissue is very important, culture conditions and cells can be conveniently and objectively evaluated by the method of the present invention, and quality control of cell products for regeneration medicine can be performed without depending on engineers' skill by the method of the present invention.

As for origin of cells to be cultured according to the present invention, the object is an animal or human living body, unless especially indicated. The object may be a healthy object, or an object who or which is desired to be treated by cultured tissue transplantation (patient). The object may be an object with skin deficit caused by burn, bedsore, ulcer, traumatic injury, or the like, or an object having a damage in the cornea due to Stevens-Johnson syndrome, bullous keratopathy, keratoconus, corneal opacity, corneal ulcer, corneal herpes, corneal degeneration (dystrophy), chemical damage or burn, or the like. If the object has a healthy tissue besides the damaged tissue, cells to be cultured can be obtained from a healthy tissue (for example, epidermis or limbus) containing stem cells originating in the object himself, herself, or itself.

The present invention is especially useful for application to epidermal keratinocytes (including epidermal keratinocyte stem cells) or a cultured tissue prepared from them (cultured skin sheet). The inventors of the present invention found that, in a cultured human epidermal keratinocyte culture system, the average locomotion speed of the cells is maximized in a colony constituted by cells of high proliferative capacity, especially a colony constituted by keratinocyte stem cells, and also found that the proliferative capacity of human epidermal keratinocyte correlates with locomotion speed thereof (Non-patent document 1 and Patent document 4). The present invention is especially useful for, besides epidermal keratinocytes, corneal epithelial cells and stratified squamous epithelial cells (including tumor cells). The expression that cells have "proliferative capacity" or "proliferation property" used for the present invention means that the cells can form a colony, and the formed colony substantially consists of cells having an ability to further proliferate, not cells that have lost or are losing proliferative capacity, unless especially indicated.

In the quality evaluation, if needed, locomotion speed may be obtained for each of a plurality of cells (for example, 2 to 100 cells) in a certain region, and a histogram may be created, or an average locomotion speed of the cells in the region may be obtained. The term region used here typically refers to a region consisting of a colony formed by cells originating in one cell. Correlation of the locomotion speed and proliferative capacity has fully confirmed for average locomotion speed of cells in one colony formed from cells inoculated at a density effective for forming colony and formed separately from other colonies, and terminal colony emerging ratio (%) observed in a system in which the foregoing colony is treated with trypsin and inoculated.

According to the method of the present invention, an evaluation method that can be performed with a combination of phase contrast microscope, digital camera, and simple image analysis program based on the present invention can be established.

According to the present invention, evaluation of cells, evaluation of culture conditions, evaluation of cultured tissue (product), etc. can be performed by using a speed histogram or cell locomotion speed (it may be average locomotion speed), and judgment criterion therefor can be appropriately defined. A reference value (also referred to as "threshold") may be defined by performing a preliminary test, or in the case of obtaining cell locomotion speed for a culture system as the object, the judgment may be performed by performing the same operation also for a control system, and comparing the locomotion speed of the culture system as the object with a value obtained for the control system.

Although the locomotion speed may be differently calculated depending on resolution of image, exposure time, whether the image is 8 bit image or 16 bit image, and so forth, it is expected that if the imaging is performed under the same conditions with maintaining the cells under predetermined culture conditions, judgment criteria commonly applicable to various cases can be obtained.

<Production of Cultured Tissue Including Quality Evaluation Step and Cell Therapy>

According to another embodiment of the present invention, a method for producing a cultured tissue including a quality evaluation step is provided. The term "cultured tissue" used for the present invention refers to a tissue model reconstructed by culturing human or animal cells outside the body, unless especially indicated. Examples of the cultured tissue include cultured epidermis, cultured corneal epithelium, and cultured cartilage. The cultured tissue may be an autologous cultured tissue.

The cultured tissue obtained by the production method of the present invention can be used for transplantation to an object for the purpose of treatment. The cultured tissue obtained by the production method of the present invention can also be a substitution for animal or simple cultured cells, and can be applied to various researches and experiments. For example, the cultured tissue can be applied to pharmacological tests, toxicity test, and so forth.

The production method of the present invention comprises at least a step (1): the step of culturing cells obtained from an object to produce a cultured tissue; and a step (2): the step of evaluating the cells obtained from the object in the culture system. The step (1) is typically the step of culturing skin keratinocytes obtained from healthy skin of an object having a wounded tissue and a healthy tissue, i.e., a patient, to prepare autologous cultured skin for transplantation to a wounded part, and the following explanations may be made for such a case. However, those skilled in the art can appropriately modify such explanations, and apply them to a case of performing the method for skin keratinocytes obtained from an object other than a patient, or a case of performing the method for cells other than skin keratinocytes.

When skin keratinocytes are cultured as the step (1), known methods for culturing epidermal cells can be applied. Those skilled in the art can appropriately design culture environment (including medium, temperature, $CO_2$ concentration, and culture period) according to the type of the cells. The cells as the object may be cultured on a layer based on feeder cells such as 3T3 cells, if it is preferred.

The production method of the present invention may comprise the step of obtaining a tissue from an object, the step of separating and/or purifying objective cells from the tissue, and the step of inoculating the obtained cells to an appropriate culture environment, in addition to the steps (1) and (2). The method may also comprise the step of taking out the produced cultured tissue from the culture system. The obtained sheet-shaped cells are transplanted to a patient. Although the step of obtaining a tissue from an object may be a medical practice, the other steps can be carried out by persons other than medical practitioners.

The step (2) of the method of the present invention can be performed before, during, or after any of the aforementioned steps without any particular restriction. In view of judging whether the cells separated from the tissue are sufficient for producing a cultured tissue, the step (2) is preferably performed after the step of separating and/or purifying the cells.

In view of evaluating quality of the cell tissue for transplantation, it is considered that the step (2) is preferably performed after or in the middle of the step (1), and before the step of taking out the cultured tissue from the culture system (before transplantation).

As another aspect of the present invention, there is provided a method for cell therapy comprising a quality evaluation step (FIG. 13). At present, quality control of cultured tissues produced for cell therapies is not substantially performed for the regeneration ability thereof. However, according to the present invention, for example, a produced cultured tissue can be monitored in real time with a phase contrast microscope, and analyzed by automatic cell tracking. If a supercomputer can be used, cell tracking and data analysis can be completed within several seconds to 1 minute. Then, a cultured tissue of good quality suitable for a treatment or transplantation can be chosen on the basis of the calculation result.

Such a system as mentioned above may specifically be the following system.

[1] A system for providing a cultured tissue for an object, the system comprising:

the step of culturing collected cells to produce a cultured tissue;

the step of performing quality evaluation of a cell tissue under culture or produced cultured tissue;

the step of choosing a cultured tissue on the basis of the result of the quality evaluation; and the step of providing the chosen quality-evaluated cultured tissue for the object.

[2] The system according to 1, wherein the quality evaluation includes cell behavior analysis.

<Evaluation of Culture Environment>

The method of the present invention can be used not only for evaluation of cells, but also for evaluation of cell culture conditions. More specifically, it can be used for analyzing presence or absence of change of behavior of cells and degree of the change at the time of changing culture conditions for a system of the cells, and judging whether the objective culture conditions are preferred to the cells or not. The culture conditions include temperature, pH, duration, presence or absence or amount of ingredients, light, and atmosphere.

For example, when whether a certain candidate ingredient is important for culture of stem cells is evaluated, behaviors of the stem cells under culture in the presence and absence of the candidate ingredient can be compared, and for example, if, when the candidate ingredient is added, locomotion speed of the cells is inferior compared with the case where the ingredient is not added, it can be estimated that the candidate ingredient may impair the stemness of the cells.

Since the method of the present invention enables evaluation of culture environment, it can be used for screening for drugs that affect behavior of stem cells. It can also be used for screening for drugs that affect infiltration and migration of cancer cells, and so forth.

BRIEF SUMMARY

Any method for non-invasively and highly precisely analyzing behavior of each of a plurality of cells did not exist so far to date. However, according to the present invention, wherein learning for cell detection using dictionary data and tracking based on a state space model are performed on the basis of the characteristics of the cells, noninvasive and highly precise evaluation of each of a plurality of cells is attained. Further, conventional management of the culture conditions for maintaining proliferation property of stem cells, and so forth depended on engineers' experiential knowledge. In the field of regeneration medicine, quality control is required for cells cultured for the purpose of transplantation as products for regeneration medicine, and so forth. Since cells for preparing a cultured tissue for transplantation usually probably differ depending on individuals from whom or which the cells have been derived, and completed cell products may have various variations, quality control of cultured tissue is very important. In such a situation, cells can be conveniently and objectively evaluated by the behavior analysis according to the present invention. Further, objective and well-reproducible quality control of products for regeneration medicine, and so forth are enabled without depending on engineers' skill.

EXAMPLES

Example 1-1

1 Continuous Observation of Epidermal Keratinocytes 1.1 Culture of Epidermal Keratinocytes Human epidermal keratinocytes originating in neonate (purchased from KURABO) were cultured under the conditions of 37° C. and 10% $CO_2$ using the mouse 3T3 fibroblasts treated with mitomycin C as feeder cells (refer to the reference [1] for details of the method).

1.2 Time-Lapse Imaging of Epidermal Keratinocytes

The cultured epidermal keratinocytes were subcultured on a 35-mm glass bottom dish, and time-lapse imaging was performed under the conditions of 37° C. and 10% $CO_2$ in which imaging was automatically performed every 5 minutes with Olympus FV10i.

2 Preparation for Tracking of Epidermal Keratinocytes

The method for tracking the epidermal keratinocytes is roughly divided into two stages, and is performed by a combination of 1) detection of cells in images, and 2) tracking using a state space model. The role of the cell detection of 1) consists of determination of initial position of the tracking and generation of observation data for the state space model with a certain time interval. For this purpose, a multi-stage cascading network is proposed. In this research, there was used an original method in which the most adjacent recognized cell existing within a circle of a certain radius starting from a predicted position was regarded as the observation data.

2.1 Image Pre-Processing

In order to make structure conspicuous, 16-bit TIFF images of 1024×1024 size outputted from a phase contrast microscope were subjected to histogram data smoothing, and changed into 8-bit PNG files of a size of 1024×1024. By using this converted images, the learning and tracking described below were performed.

2.2 Dictionary Creation

Since a mechanical learning method is used for detection and recognition of cells in this research, data for learning (dictionary) are needed. Here, rectangle regions chosen for cell nuclei by human naked eyes on phase contrast microscope images such as shown in FIG. 1 are called dictionary. Such a dictionary was prepared with 188 images in a rectangle region number of 18032. Regions not corresponding to the cells were also enclosed with rectangles in a number of 5628.

2.3 Learning for Cell Detection

2.3.1 Extraction of Candidate Region for Cell Position (First Stage)

In order to perform detection of cell position, a model of deep learning called SSD[2] recently proposed was used as an algorithm for material detection. Before the learning, flip vertical and flip horizontal (4 times), gamma correction (0.75, 1.00, 1.25, and 1.50), and change of resolution (0.75, 0.85, 1, 1.15, and 1.25 times) were performed as data extension to extend the data of the original 188 images 80 times (=4×4×5) to 15040 images.

2.3.2 Determination of Position of Cell (Second Stage)

The candidate regions extracted by SSD in the first stage in fact included many regions not corresponding to cells. Then, in order to distinguish regions of cells from these candidate regions with high precision, three kinds of deep convolution networks based on VGG16[3] and classified into the class 2 were prepared (refer to FIG. 3), and judgment was performed by constructing a cascading network consisting of these models combined in multiple stages as shown in FIG. 4.

The three kinds of convolution networks (DCN1, DCN2, and DCN3) were independently made to learn. For the learning, data extension was performed by rotating the images of the rectangle regions in the dictionary images in a unit of 5 degrees per one time to increase the data 72 times. As images of cells, such images of cells at the mitotic phase (Mitotic) as shown in FIG. 2 were also added. The numbers of these rectangle regions used for the learning are summarized in the following table. At the time of the learning, data extension was performed by such correction that the gamma value should become any one of 0.75, 1.00, 1.25, and 1.50 at a probability of ½ at random. Adam[4] was used as the optimization algorithm, and the cascading network was constructed by using Chainer[5].

TABLE 1-1

Number of cell rectangles used for learning of second stage

| | Original image | After rotation | Training image | Class label |
|---|---|---|---|---|
| Positive | 18032 | 1298304 | 1308888 | Cell |
| Mitotic | 147 | 10584 | 405216 | Negative |
| Negative | 5628 | 405216 | | |

For the learning, the supercomputer of Information Technology Center, The University of Tokyo (Reedbush-L) was used for the calculation.

2.4 Tracking Method

As the algorithm for tracking of every single epidermal keratinocyte, a linear state space model described with the observation equation and state equation shown below was used.

$$z_t = Hx_t + v_t \quad \text{[Equation 10]}$$

$$x_t = Fx_{t-1} + w_t$$

$$x_t = \begin{bmatrix} x_t \\ y_t \\ u_t \\ v_t \end{bmatrix}, F = \begin{bmatrix} 1 & 0 & 1 & 0 \\ 0 & 1 & 0 & 1 \\ 0 & 0 & 1 & 0 \\ 0 & 0 & 0 & 1 \end{bmatrix},$$

$$z_t = \begin{bmatrix} z_{x,t} \\ z_{y,t} \\ z_{u,t} \\ z_{v,t} \end{bmatrix}, H = \begin{bmatrix} 1 & 0 & 0 & 0 \\ 0 & 1 & 0 & 0 \\ 0 & 0 & 1 & 0 \\ 0 & 0 & 0 & 1 \end{bmatrix}$$

In the equations, $x_t$ represents a state vector, $(x_t, y_t)$ represents coordinate of a cell at a time point t, and $(u_t, v_t)$ represents a speed vector of the cell at the time point t. F is a transition matrix, and H is an observation matrix. $z_t$ is an output vector corresponding to $x_t$. $v_t$ and $w_t$ represent a Gaussian white noise vector. This linear state space model is updated by using a Kalman filter[6].

The method for preparing observation data at the time of the tracking using a Kalman filter was as follows. Coordinate of a most adjacent cell within a distance of a radius of 20 pixels (actual distance is about 12 μm) from the predicted coordinate $(x_t+1, y_t+1)$ was used as observation value, and when a cell did not exist within a distance of a radius of 20 pixels, data were considered missing.

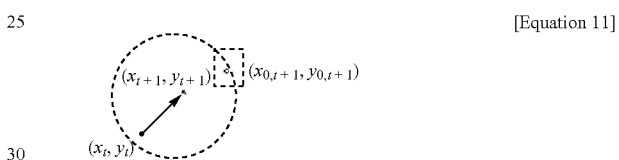

[Equation 11]

The cell enclosed in □ serves as an observation cell at a time point t+1. When any recognized cell is not observed within the range of a radius of 20 pixels, data were regarded missing.

3 Tracking Method

3.1 Preparation of Input Data

A plurality of images obtained about every about 5 minutes were prepared, and subjected to histogram data smoothing.

3.2 Cell Detection

FIG. 5-1 shows detection of cell regions performed by inputting the candidate regions obtained with the cell detector in the first stage into a high precision cell distinction apparatus in the second stage.

An example of actual cell detection using a cascading cell detector is shown in FIG. 6 as a flowchart.

3.3 Tracking

Tracking using a Kalman filter was performed by using coordinate of a most adjacent cell within a radial distance of 20 pixels from a predicted coordinate as the observed value, and regarding that data were missed when any cell was not found within the radial distance of 20 pixels. FIG. 7 shows examples of determination of an observation cell and data missing at contiguous two time points. The lower circle indicates an example of the case that position of a cell (star) is found in the observation range of the predicted position (white spot) at a certain time point. By using coordinate of the star in this circle as observation data, filter distribution of the Kalman filter is updated. On the other hand, the upper circle indicates an example of the case that coordinate is not found in the observation range, and in this case, data are considered missing, and the process advances to the following time step without performing the filtering.

Independent tracking of each single cell according to such a principle is shown in FIG. 8.

An example of tracking of many cells is then shown. In the example shown in FIG. 9, trajectories of every single cell are drawn. FIG. 10 shows a diagram that should be called space-time diagram of cells, and trajectories of the cells are plotted as three-dimensional trajectories, in which the time axis is in the height direction. In the case of this example, it can be seen that the cells show movement like rotation as aggregates.

3.4 Creation of Speed Histogram

If norms of the obtained speed vectors at all the times points are added and divided with the time, average locomotion speed of the cell can be obtained. This calculation was performed for each cell, and a histogram was created (FIG. 11).

The result shown by this histogram indicates that, in the cell population of this colony, a major part of the cells moved at a speed of about 30 to 35 μm/h. This value is very close to the value reported in Patent document 5, and indicates that locomotion speed of a large number of cells can be automatically measured by the method of the present invention at the same precision as that of the manual measurement of the cell locomotion speed. Since Patent document 5 reported that the average value of the cell locomotion speeds in this colony positively correlated with proliferative activity of human epidermal keratinocytes, from such a histogram and average of cell locomotion speed calculated from it, human epidermis keratinocyte stem cell colony that shows extremely high proliferative activity can be identified.

Example 1-2

Tracking of cells was performed in the same manner as that of Example 1-1 except for the following points.

2 Preparation of Tracking of Epidermal Keratinocytes 2.3 Learning for Cell Detection 2.3.1 Extraction of Candidate Region of Cell Position For detection of cell position, a model of deep learning called SSD[2] proposed as an algorithm for material detection was used. A model conceptual diagram of SSD is shown in FIG. 3-2.

2.3.2 Determination of Position of Cell

The candidate regions extracted by SSD in the first stage included many regions not corresponding to cells. Then, in order to distinguish regions of cells from these candidate regions with high precision, two kinds of networks based on CapsNet and classified into the class 2 were prepared (refer to FIG. 3-3), and judgment was performed by constructing a cascading network consisting of these models combined in multiple stages as shown in FIG. 4-2. The two kinds of networks (CpasNet1 and CapsNet2) were independently made to learn. For the learning, data extension was performed by rotating the images of the rectangle regions in the dictionary in a unit of 5 degrees per one time and performing gamma correction (0.75, 0.85, 1.00, 1.15, and 1.25) to increase the data 360 (72×5) times. The numbers of these rectangle regions used for the learning are summarized in the following table.

Adam[4] was used as the optimization algorithm for the learning, and the cascading network model was constructed by using Chainer[5].

TABLE 1-2

Number of rectangle regions used for learning of second stage

| | Original image | After rotation | After gamma correction | Training image | Class label |
|---|---|---|---|---|---|
| Positive | 18032 | 1298304 | 6491520 | 6544440 | Cell |
| Negative | 5628 | 405216 | 2026080 | 2026080 | Negative |

3 Tracking Method

The method for tracking epidermal keratinocytes is roughly divided into two stages, and is performed by a combination of 1) detection of cells in images, and 2) tracking using a state space model. The role of the cell detection of 1) consists of determination of initial position of the tracking and generation of observation data for the state space model at each time point. For this purpose, a multi-stage cascading network is proposed. In this method, there was used an original method in which the forward most adjacent recognized cell existing within a circle of a certain radius starting from a predicted position was regarded as the observation data.

3.1 Input Data

Colony images of epidermal keratinocytes were prepared, and subjected to histogram data smoothing.

3.2 Extraction of Cell Coordinate Candidate Region

In detection of candidate region, an image in a size of 1024×1024 was divided into 9 pieces in a size of 341×341, and divided into 16 pieces in a size of 256×256 to create total 25 regions (see FIG. 5-2). The created regions were resized into a size of 300×300, and inputted into SSD, and candidate regions were outputted. For the regions detected by SSD, confidence error $L_{conf} \in [0,1]$ is calculated as likelihood indicating likelihood for the region to correspond to a cell. In this research, a detected region that satisfied the following condition for $L_{conf}$:

$$L_{conf} > 0.01 \qquad \text{[Equation 12]}$$

was extracted as a candidate region of cell.

3.3 Determination of Cell Coordinate

The candidate regions extracted by SSD in the first stage in fact included many regions that did not correspond to cells. Therefore, in order to distinguish regions of cells from these candidate regions with high precision, two kinds of deep convolution networks based on CapsNet and classified into the class 2 were prepared, and judgment was performed by constructing a cascading network consisting of these models combined in multiple stages as shown in FIG. 4-2.

The candidate regions judged to correspond to cells included many overlapping regions. Therefore, a region having a center coordinate existing within a radial distance of 20 pixels from the center coordinate of a region judged to correspond to a cell was determined to overlap, a region having a center coordinate not existing within a radial distance of 20 pixels was determined not to overlap, and for the overlapping regions, the center coordinate of the region that showed the highest likelihood to correspond to a cell as determined with a distinction apparatus was used as the coordinate of the cell. As for examples of overlapping cell, FIG. 7 can be referred to. The markers indicate examples of center coordinates of the detected regions of cells. Circles having a radius of 20 pixels are shown in white. The lower white dot indicates an example of a cell detected in duplicate. The radius of the circle was set to be 20 pixels, since the size of the rectangular region of one cell was about 30 to 40 pixels.

3.3 Tracking Method

In this step, a method for independently tracking each one single human epidermal keratinocyte is constructed by using a general state space model.

$$x_t = f_t(x_{t-1}) + \omega_t$$

$$z_t = h_t(x_t) + v_t \quad \text{[Equation 13]}$$

In the equations, $x_t$ represents a speed vector:

$$x_t = \begin{pmatrix} x_t \\ y_t \\ v_{x,t} \\ v_{y,t} \\ a_{x,t} \\ a_{y,t} \end{pmatrix} \quad \text{[Equation 14]}$$

wherein $(x_t, y_t)$ represents coordinate of a cell at a time point t, $(v_{x,t}, v_{y,t})$ represents a speed vector of the cell at the time point t, and $(a_{x,t}, a_{y,t})$ represents acceleration of the cell at the time point t. $z_t$ is an output vector corresponding to $x_t$. $v_t$ and $w_t$ represent a noise component. This general state space model is updated by using an ensemble Kalman filter.

A conceptual diagram of the tracking using an ensemble Kalman filter is shown in FIG. 8. In the data generation at the time of this tracking, coordinate of a most adjacent cell within a distance of a radius of 20 pixels from a predicted coordinate is first set to be a candidate coordinate of observation value, and when a cell does not exist within a distance of a radius of 20 pixels, data are considered missing. Then, an inner product of a unit vector of the speed vector at the candidate coordinate of observation, $$\frac{v_c}{\|v_c\|}, \quad \text{[Equation 15]}$$

and a unit vector of the speed vector of the predicted value $$\frac{v_p}{\|v_p\|}, \quad \text{[Equation 16]}$$

$$\left(\frac{v_p}{\|v_p\|}, \frac{v_c}{\|v_c\|}\right) \quad \text{[Equation 17]}$$

is calculated, and when it satisfies the condition $$0 < \left(\frac{v_p}{\|v_p\|}, \frac{v_c}{\|v_c\|}\right) < 1, \quad \text{[Equation 18]}$$

this candidate value is used as the observation value in the tracking.

[Equation 19]

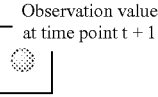
Observation value at time point t + 1

Predicted coordinate at time point t + 1

Coordinate at time point t

The cell enclosed in the rectangle serves as an observation cell at the time point t+1. When any recognized cell is not observed within the range of a radius of 20 pixels, data are regarded missing. In FIG. 12, the flow of this tracking is shown as a flowchart. Tracking was independently performed for each cell according to such a principle.

Like Example 1-1, all the detected cells were independently tracked, and images showing trajectory, a space-time diagram drawing trajectories of each of many cells, and a speed histogram were created. Roughly the same, but somewhat improved results compared with the results of Example 1-1 (FIGS. 8 to 11) were obtained.

Example 2: Monitoring of Culture Conditions

The automatic tracking system was applied to monitoring of culture conditions of epidermal keratinocytes (obtained and cultured in the same manner as that of Example 1-1).

Behaviors of epidermal keratinocytes under different culture conditions were compared in the same manner as that of Example 1-2. The cell locomotions were compared. Those of the case where the medium was exchanged on the day 4 of the culture (feeding) and the case where the medium was not exchanged (no feeding) were compared. When the colonies were observed on the day 5, the cells were significantly moving in the system where the medium was exchanged. In contrast, the cells did not move so much in the system where the medium was not exchanged. In the lower diagrams of FIG. 14, positions of the nuclei at each time point are shown with lines.

In the culture system of the inventors of the present invention, epidermal keratinocytes show a spiral migration pattern in colonies. As clearly seen from FIG. 15, the trajectory lines in 2D images (upper side) and 3D images (lower side) twisted. However, when 10 ng/ml of epidermal growth factor (EGF) (Up state, #01-107) was added to the medium, the migration pattern changed. As previously reported[7], EGF induces migration of epidermal keratinocytes to the outside. By the automatic tracking with this system, migration pattern could be seen. Interestingly, the migration speed did not change. EGF changed only the direction of migration in a short period of time.

By the automatic tracking, it could be clearly verified and analyzed that culture conditions affect cell behaviors. This system can be applied to monitoring of culture conditions for cells.

Example 3: Evaluation of Sternness

The automatic tracking system was applied to prediction of stem cell colonies. Two epidermal keratinocyte colonies were cloned, speed information thereof was obtained by automatic tracking in the same manner as that of Example 1-2, and motion index (MI) was calculated from the obtained speed information. The motion index (MI) mentioned here is a value obtained by dividing average speed of cells in the inside region of colony with average speed of cells in the outside region of the colony, i.e., motion index (MI) is [average speed of cells in inside region of colony]/[average speed of cells in outside region of colony].

The inside region and the outside region were defined as follows.
(1) First, create a mask image that specifies a region of whole colony (whole colony is actually manually chosen).
(2) Then, create another mask image by reducing the created mask image to 0.65 time, and overlap it on the mask image created first. At this time, overlap it so that the centers of gravity of the two images should agree with each other.
(3) Define the center of the stacked images (part of the mask image created by the reduction) to be the inside region of colony, and the other part to be the outside region.

Although these two colonies had substantially the same morphology, they showed different proliferative capacities. One of the colonies showed MI of 0.7, and thus had no possibility of long-term proliferation. Such a clone is called paraclone. In contrast, the other colony showed MI of 1.02, and could maintain significant proliferative capacity. Such a clone is called holoclone. The paraclone is a cell that can only temporarily proliferate, and the holoclone is a cell having a long-term proliferative capacity, i.e., a stem cell. There were analyzed 35 colonies, and it was confirmed that colonies showing a low MI mainly originated in paraclones, and the ratio of holoclone increased with increase of MI (FIG. 16).

It is desirable that whether a cell is a stem cell or not can be correctly predicted. By automatic tracking, colony originating in holoclone could be distinguished, i.e., it could be determined that the colony was a stem cell colony. This system can be applied to selection of a stem cell, and evaluation of sternness.

Example 4: Evaluation of ES Cell

The automatic tracking system was applied to ES cells.
The culture protocol of mouse ES cell is shown below.
(1) Coat a culture dish with a 0.1% gelatin solution (Biological Industries, 01-944-1B).
(2) Inoculate mouse embryonic fibroblasts (MEF, established in the Nishimura laboratory) on the gelatin-coated dish, and culture them at 37° C. and 5% $CO_2$ for 4 hours.
(3) Then, inoculate mouse ES cells (established in the Nishimura laboratory), and culture them at 37° C. and 5% $CO_2$. The culture liquid for mouse ES cells had the following composition.
Mouse ES basal medium (Biological Industries, 01-171-1)
0.5 nM LIF human recombinant culture supernatant (Wako, 129-05601)
0.1 mM 2-Mercaptoethanol (SIGMA, M3148)

The mouse ES cells were tracked in the same manner as that of Example 1-2. A dictionary for ES cells was created, and the imaging interval was 5 minutes. The results are shown in FIGS. 17 to 19. It was revealed that locomotion ability of ES cells is lower than that of epidermal keratinocytes.

This system can be widely applied to evaluation of stem cells such as ES cells.

REFERENCES CITED IN THE SPECIFICATION

[1] Nanba, D., et al., Cell motion predicts human epidermal sternness, J. Cell Biol., 2015: p. jcb. 201409024

[2] Liu, W., et al., Ssd: Single shot multibox detector, in European conference on computer vision, 2016, Springer
[3] Simonyan, K. and A. Zisserman, Very deep convolutional networks for large-scale image recognition, arXiv preprint arXiv:1409.1556, 2014
[4] Kingma, D. P. and J. Ba, Adam: A method for stochastic optimization, arXiv preprint arXiv:1412.6980, 2014
[5] Tokui, S., et al., Chainer: A next-generation open source framework for deep learning, in Proceedings of workshop on machine learning systems (LearningSys) in the twenty-ninth annual conference on neural information processing systems (NIPS), 2015
[6] Kalman, R. E., A new approach to linear filtering and prediction problems, Journal of Basic Engineering, 1960, 82 (1): p. 35-45
[7] Nanba et al., EMBO Mol. Med., 5:640-653, 2013, Actin filament dynamics impacts keratinocyte stem cell maintenance

The invention claimed is:
1. A method for analyzing behavior of cells, the method comprising:
providing a dictionary containing previously-captured image data of cell nuclei of the cells;
obtaining time-lapse images of the cells to be analyzed and extracting candidate regions from the time-lapse images;
detecting positions of the cells in a cell region for every frame of the time-lapse images, while selecting from the candidate regions the cell region as a region that contains the cells based on the dictionary containing the previously-captured image data of the cell nuclei; and
tracking each cell by using a state space model using a position of a most adjacent cell within a predetermined distance from a predicted position of the cell as observation data.
2. The method according to claim 1, wherein the tracking step uses a position of a forward most adjacent cell within a predetermined distance from the predicted position as the observation data.
3. The method according to claim 2, wherein the determination is performed by using deep learning.
4. The method according to claim 1, wherein, in the tracking step, when any cell is not found within the predetermined distance from a predicted position, the data are considered missing.
5. The method according to claim 1, wherein the cell is a stem cell.
6. The method according to claim 5, wherein interval of previous time and present time for capturing the time-lapse images is 2 to 15 minutes.
7. The method according to claim 1, which is used for quality evaluation of a cultured tissue for cell therapy.
8. A method for evaluating quality of a cultured tissue containing cells, the method comprising:
providing a dictionary containing previously-captured image data of cell nuclei of the cells;
obtaining time-lapse images of the cells to be analyzed and extracting candidate regions from the time-lapse images;
detecting positions of the cells in a cell region for every frame of the time-lapse images, while selecting from the candidate regions the cell region as a region that contains the cells based on the dictionary containing the previously-captured image data of the cell nuclei;
tracking a position of each cell by using a state space model using a position of a most adjacent cell within a predetermined distance from a predicted position of the cell as observation data; and calculating speed information of each cell on the basis of tracking information obtained in the tracking step and evaluating the quality of the cultured tissue on the basis of the speed information.

9. A method for producing a cultured tissue and evaluating quality of the cultured tissue, the method comprising:

culturing cells obtained from an object to prepare a cultured tissue for transplantation; and evaluating the prepared cultured tissue by using locomotion information of the cells contained in the cultured tissue as an index; and wherein the method further comprises an evaluation step which comprises:

detecting positions of a plurality of the cells for every frame of time-lapse images of all or a part of the cultured tissue;

tracking each cell by using a Kalman filter of which observation data is a position of a most adjacent cell within a predetermined distance from a predicted position of the cell at present time, which is the position of the cell in the frame of previous time point; and calculating locomotion information of each cell on the basis of tracking information obtained in the tracking step and evaluating the quality of the cultured tissue on the basis of the locomotion information.

10. The method according to claim 9, wherein the cultured tissue is cultured epidermis, cultured corneal epithelium, or cultured cartilage.

* * * * *